(12) United States Patent
Nabity et al.

(10) Patent No.: US 6,354,345 B1
(45) Date of Patent: Mar. 12, 2002

(54) PUMPING SYSTEM

(75) Inventors: Frederick Alan Nabity; Robert Raymond Fiedler; James Paul Masek; Brian D. Dawson; Russell Todd Barker; Frederick Detlef Sueverkruepp, III; Ralph E. Setter, all of Lincoln; Paul George Wright, Garland; Larry Lee Fritz, Lincoln, all of NE (US)

(73) Assignee: Isco, Inc., Lincoln, NE (US)

(*) Notice: Subject to any disclaimer, the term of this patent is extended or adjusted under 35 U.S.C. 154(b) by 0 days.

(21) Appl. No.: 09/340,882

(22) Filed: Jun. 28, 1999

Related U.S. Application Data

(62) Division of application No. 08/597,284, filed on Feb. 6, 1996, now Pat. No. 5,915,932, which is a continuation-in-part of application No. 08/387,595, filed on Feb. 13, 1995, now Pat. No. 5,576,503, which is a continuation-in-part of application No. 08/120,724, filed on Sep. 13, 1993, now abandoned, which is a division of application No. 07/807,200, filed on Dec. 16, 1991, now Pat. No. 5,401,139, which is a division of application No. 07/474,154, filed on Feb. 2, 1990, now Pat. No. 5,125,801.

(51) Int. Cl.[7] .................................................. B65B 3/00
(52) U.S. Cl. ........................................ 141/284; 141/130
(58) Field of Search ................................ 141/130, 284; 73/863.01, 863.02, 863.03, 864.31, 864.34, 864.35, 864.22, 864.24, 864.25; 422/63, 64, 67

(56) References Cited

U.S. PATENT DOCUMENTS

| | | | |
|---|---|---|---|
| 3,751,990 A | 8/1973 | Blechman | ................... 141/130 |
| 3,908,761 A | 9/1975 | Patterson | |
| 3,924,471 A | 12/1975 | Singer | ......................... 141/130 |
| 3,927,701 A | 12/1975 | Lederer | ......................... 141/98 |
| 4,415,011 A | * 11/1983 | Grant | ......................... 141/284 |
| 4,702,679 A | * 10/1987 | Malbec | ........................ 417/475 |
| 4,950,136 A | * 8/1990 | Haas et al. | ................. 417/477 |
| 4,995,432 A | * 2/1991 | Tervamaki et al. | ......... 141/130 |
| 5,168,763 A | * 12/1992 | Stewart | ........................ 141/130 |
| 5,645,114 A | * 7/1997 | Bogen et al. | ................. 422/64 |

FOREIGN PATENT DOCUMENTS

| | | |
|---|---|---|
| FR | 2 475 646 | 2/1981 |
| GB | 2 223 217 A | 4/1990 |
| WO | WO 91/04939 | 4/1991 |
| WO | WO 92/08963 | 5/1992 |
| WO | WO 95/02176 | 1/1995 |

* cited by examiner

*Primary Examiner*—J. Casimer Jacyna
(74) *Attorney, Agent, or Firm*—Vincent L. Carney

(57) ABSTRACT

To pump fluid into sample containers, a distributor arm of a sample collector is calibrated as to position in a computer memory and is moved from position to position over different containers while a counter in computer memory keeps track of its position. When the distributor arm is over the designated container, samples are pumped into the container. To pump the fluid into the container, the rollers of a peristaltic pump are supported to prevent the rollers from compressing the tube more than the thickness of the walls of the tube. A tube holder rotates along with the roller assembly of the peristaltic pump and keeps the tube in line with the rollers.

4 Claims, 16 Drawing Sheets

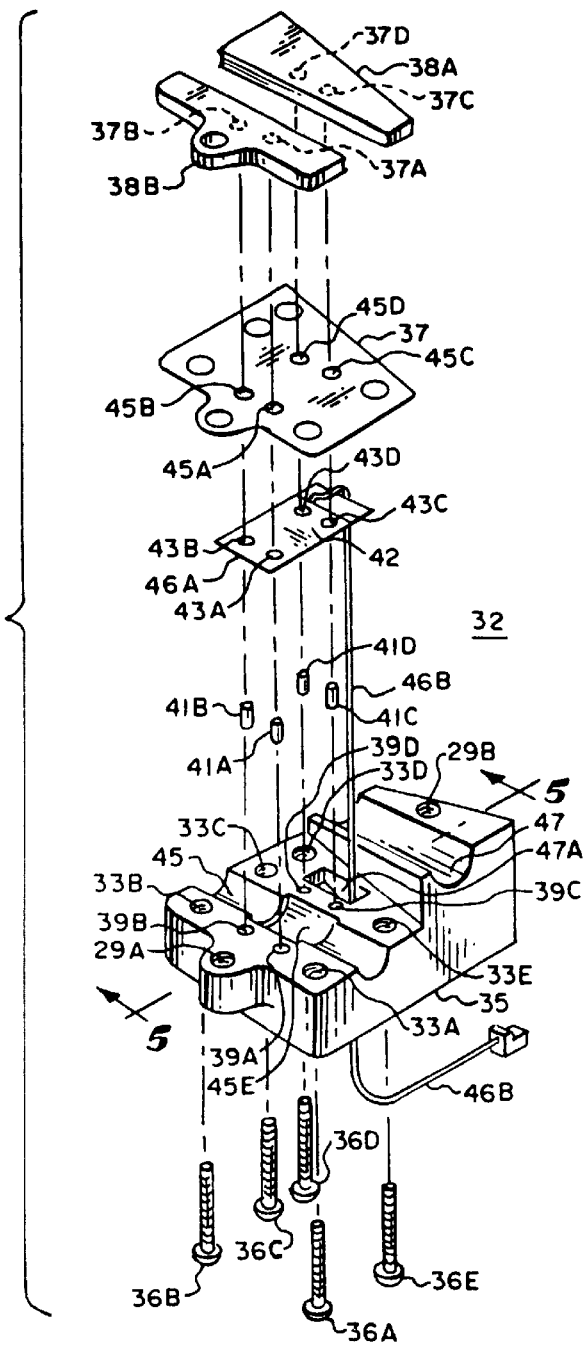
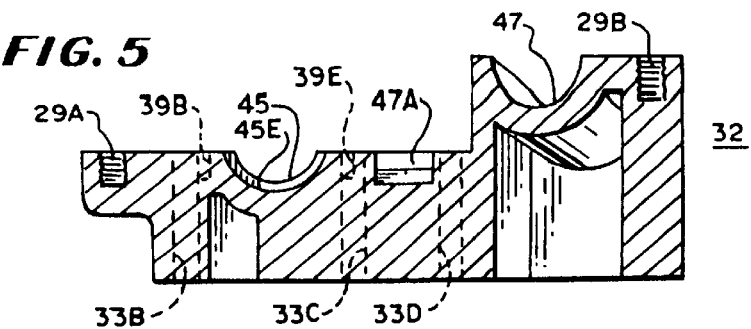

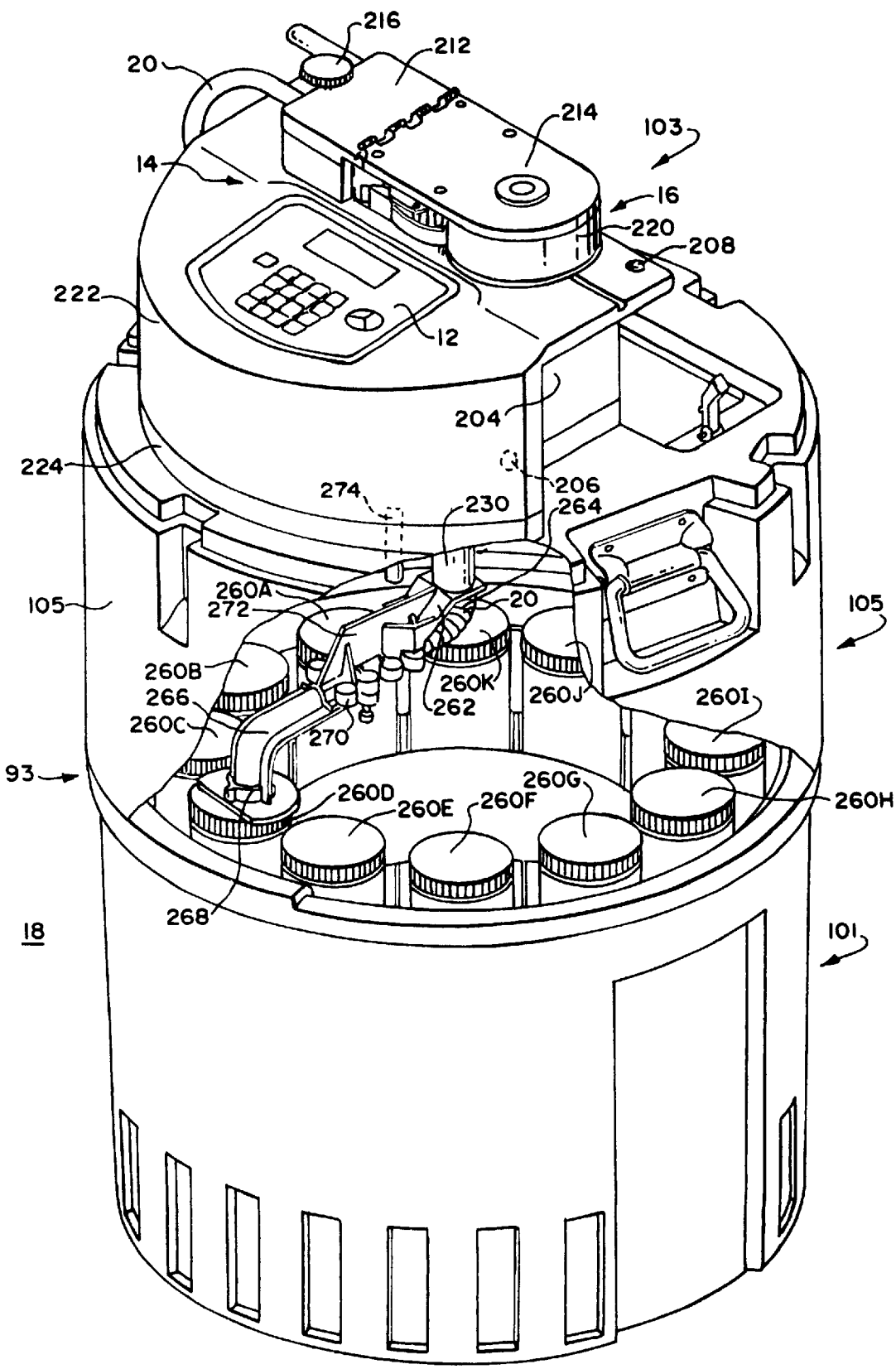

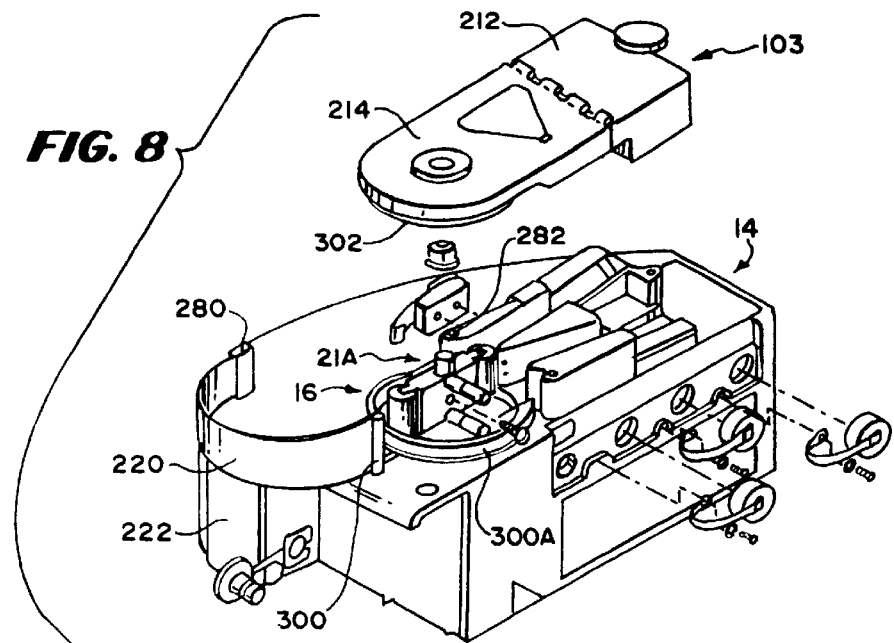
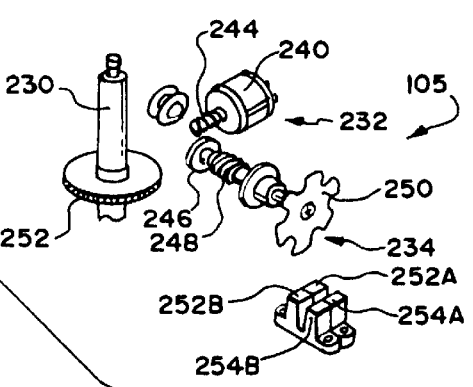
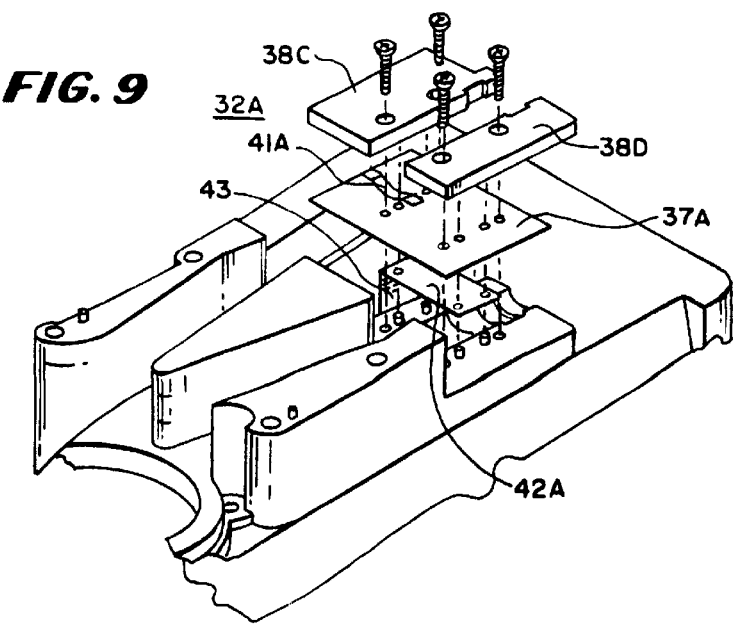

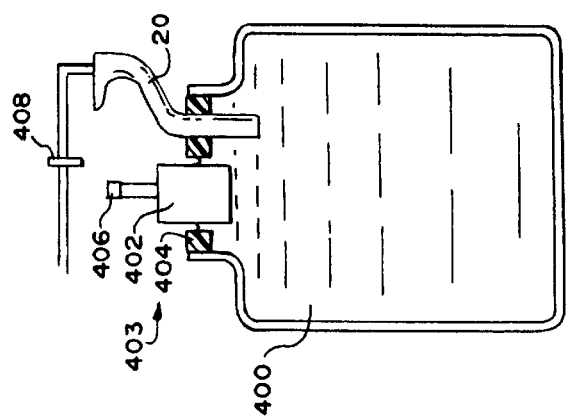
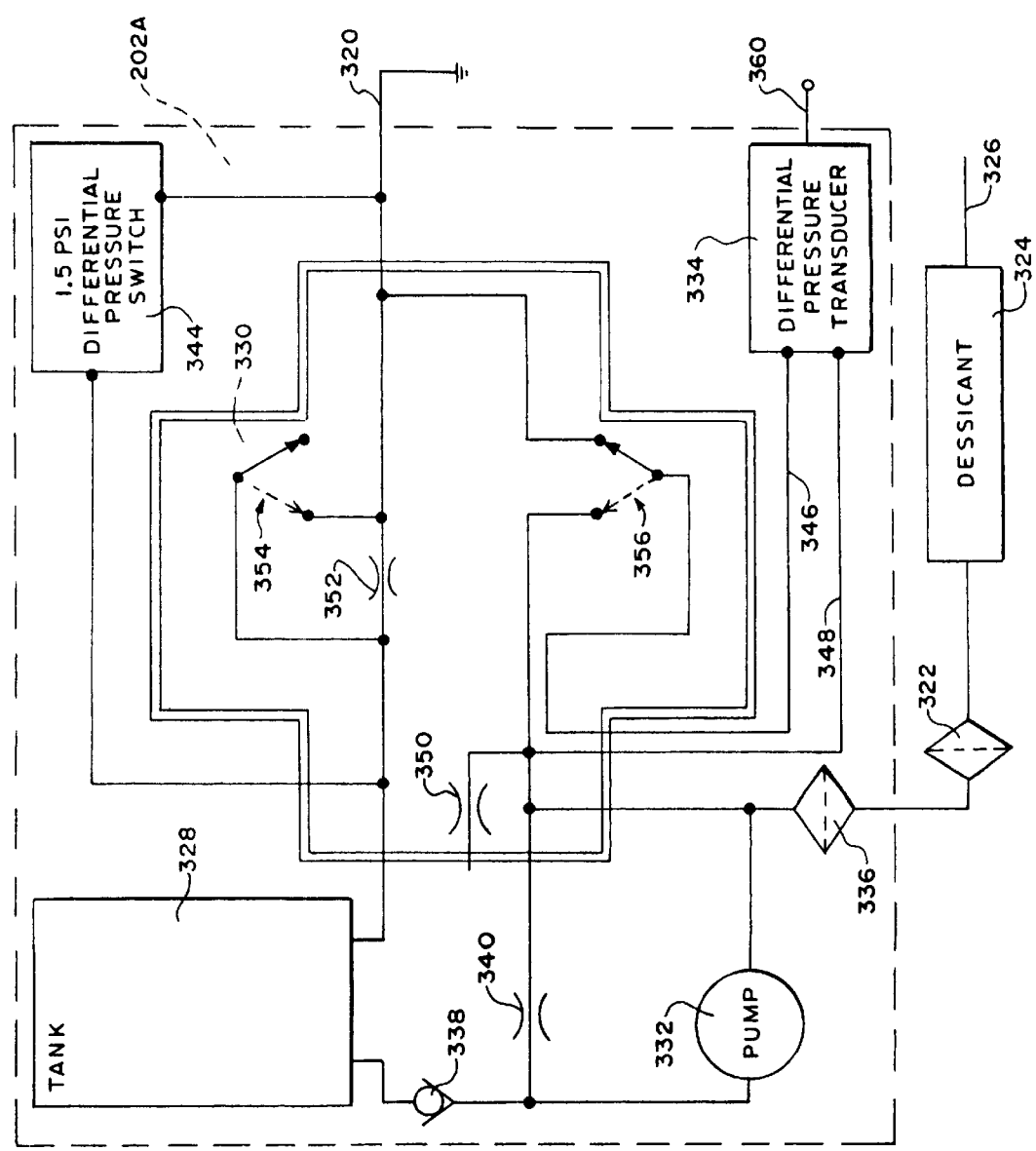

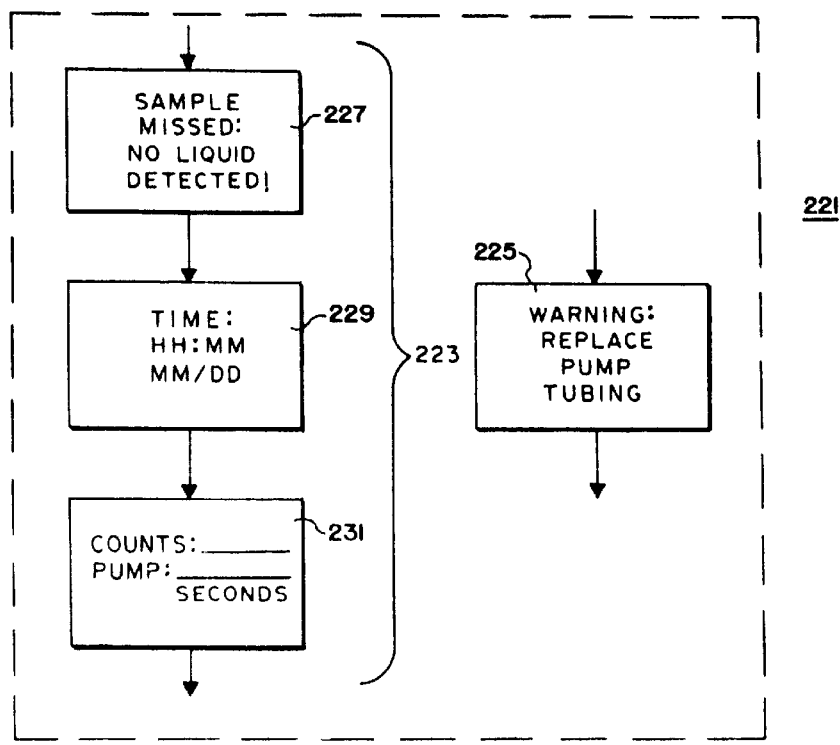
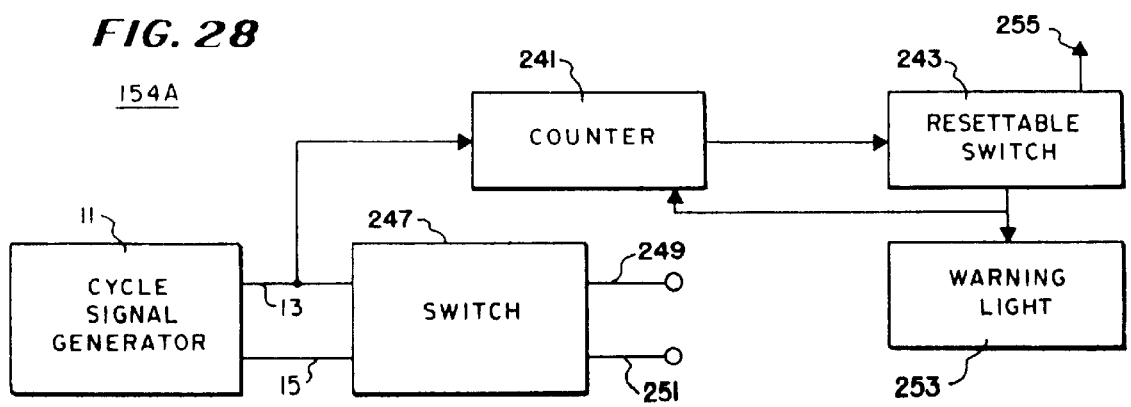

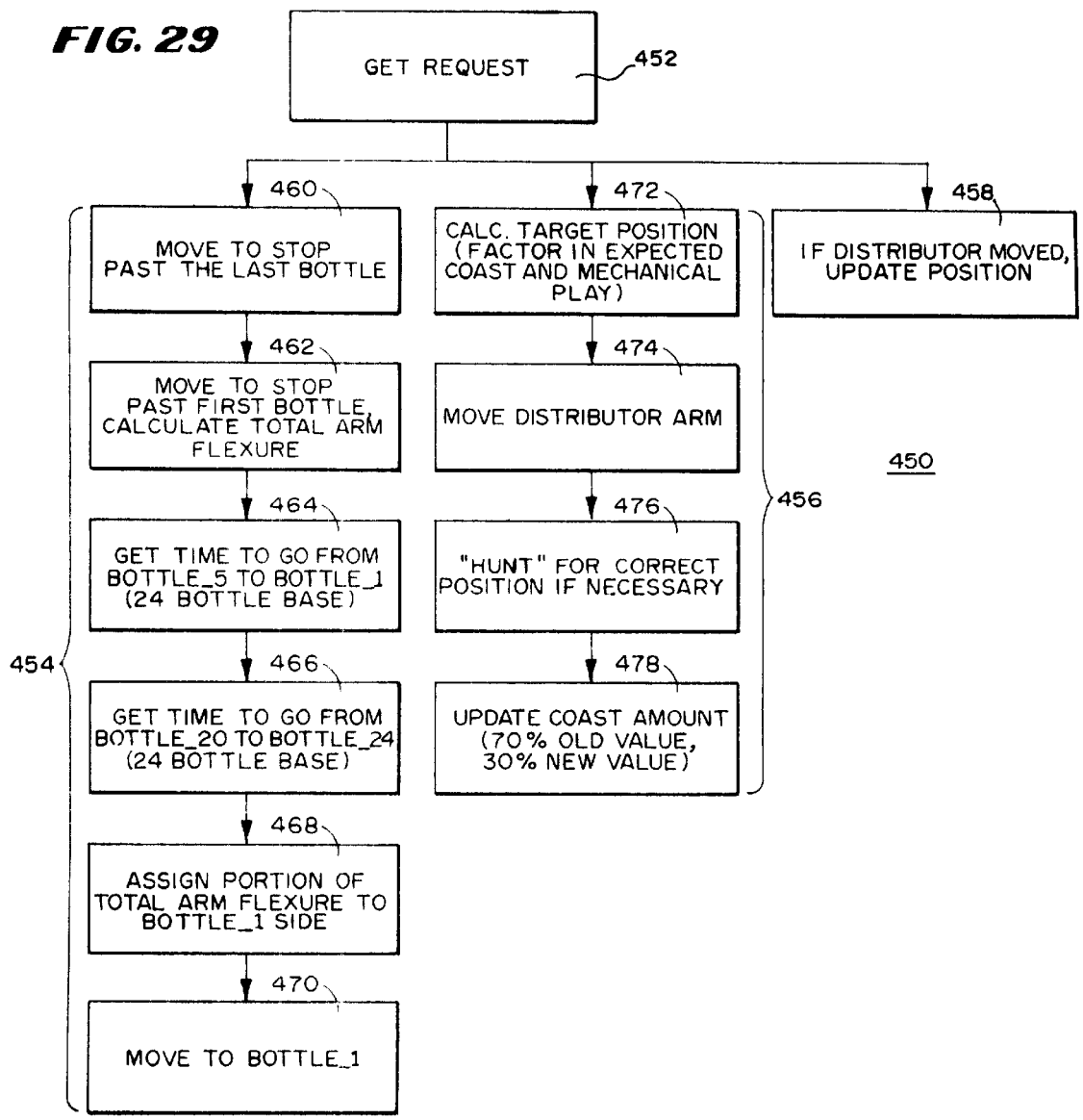

PUMPING SYSTEM

RELATED CASES

This application is a divisional of U.S. parent application Ser. No. 08/597,284 filed Feb. 6, 1996, now U.S. Pat. No. 5,915,932 which is a continuation-in-part of U.S. application Ser. No. 08/387,595, filed Feb. 13, 1995, now U.S. Pat. No. 5,576,503, which is a continuation-in-part of U.S. application Ser. No. 08/120,724, filed Sep. 13, 1993, now abandoned, which is a divisional application of U.S. application Ser. No. 07/807,200, filed Dec. 16, 1991, now U.S. Pat. No. 5,401,139, which is a divisional of U.S. application Ser. No. 07/474,154 filed Feb. 2, 1990, now U.S. Pat. No. 5,125,801 in the names of Frederick Alan Nabity, Paul George Wright, Raymond Hulinsky and Douglas Timothy Carson for PUMPING SYSTEM and assigned to the same assignee as this application.

BACKGROUND OF THE INVENTION

This invention relates to pumping systems and more particularly to pumping systems that draw samples from a source of liquid.

It is known from U.S. Pat. No. 4,415,011 to Douglas M. Grant, issued Nov. 15, 1983, and from U.S. Pat. No. 4,660,607 to Carl D. Griffith, issued Apr. 28, 1987, to pump liquids from a liquid source through a peristaltic pump into sample containers. In such system, the liquid is pumped through a flexible tube, the location of the liquid in the tube is sensed and it is metered into sample containers. The tube is subjected to flexing by rollers at a rate intended to deposit a predetermined sample volume into preprogrammed containers arranged in a sample tub. A distributor may move a nozzle over the appropriate sample bottle to deposit the sample therein. The distributors usually follow one predetermined path.

In the prior art samplers of this type, the peristaltic pumps are generally mounted horizontally with a horizontal axis of rotation for the roller assembly and fasteners such as bolts or screws must be removed to obtain access to the interior of the pump. The distributor only follows a continuous path and stops at mechanically fixed positions to deposit samples. Equipment used for triggering the taking of samples such as flow meters in stand alone equipment for such measurements.

These prior art samplers have several disadvantages such as for example: (1) under some circumstances, the tubes may travel laterally out of position within the peristaltic pump, resulting in a decrease in efficiency and increase in wear on the tube; (2) the pump may be unable to pump at the desired flow rate when there is a large head of pressure; (3) the tube within the pump may be subject to excessive wear; (4) it is difficult to change the peristaltic pump tube; (5) there may be occasions in which the outlet port of the sampler does not align in a satisfactory manner with the container to provide liquid therein; (6) there is insufficient flexibility in the movement of the distributor; (7) the samples may under some circumstances be tampered with to avoid detection of of some water conditions; and (8) the equipment used in cooperation with the sampler is excessively bulky and expensive.

SUMMARY OF THE INVENTION

Accordingly, it is an object of the invention to provide a novel liquid sampler.

It is a further object of the invention to provide a novel pumping system.

It is a still further object of the invention to provide a pumping technique which provides higher average line velocity under a head of pressure.

It is a still further object of the invention to provide a pumping system that permits easy changing of tubes;

It is a still further object of the invention to provide a peristaltic pump in which the tubes within the peristaltic pump have a longer life;

It is a still further object of the invention to provide a sampler which is able to deposit samples at random time intervals in containers in order to avoid tampering;

It is a still further object of the invention to provide a sampler having a distributor for distributing samples into bottles in which the resolution of the position of the distributor is accurately programmably controllable;

It is a still further object of the invention to provide a sampler in which different modules such as bubbler modules or data processing modules may be attached;

It is a still further object of the invention to provide a novel sampling technique in which better registration of the outlet nozzle with the sample container is provided.

In accordance with the above and further objects of the invention, a sampler includes: (1) a peristaltic pump that is mounted horizontally with a vertical axis of rotation of the roller assembly for easy insertion of pump tubing, has a tube aligning system to reduce creeping and peristaltic pump tube wear, a pump tube through which liquid is drawn at a higher average velocity, particularly when the speed of pumping cooperates with the pump tubing energy of restoration; (2) a distributor that has improved registration with containers to receive samples from the pump; and (3) is able to deposit samples in bottles having random time intervals under program control for security reasons.

The peristaltic pump housing is mounted to rotate the rollers in a horizontal plane about a vertical axis. One side of the pump housing is opened easily to expose the rollers for easy insertion of tubing. The rollers are designed with guides to avoid moving the tubing out of position and in one embodiment, are spring biased against a platen to avoid crushing the tubing. A safety check is provided by a magnet and reed switch to prevent the pump motor from operation when the pump housing is open.

The tubes are specially constructed to cooperate with the pump motor for maximum efficiency by utilizing a speed and energy of restoration that maximizes vacuum force on the liquid. For this purpose, the hose is specially cured for stability and a thickness is selected to provide a coefficient of restoration that increases the vacuum pressure. The pump is operated at a speed in which the energy of restoration is sufficient to restore the shape of the tube between compression at relatively high speed and may pull water under a twenty-four foot head with a velocity of two feet per second. The housing accommodates modules connected to sensors for transmitting sensed values and for recording them.

In operation, the nozzle of the distributor is adjustable in position and may be programmed with precision to register with bottles of different sizes and at different locations. For zeroing, the distributor is moved in a first direction against a stop and then rotated in the opposite direction to press against the stop from the opposite side. The play between the two caused by pressure against the stop is measured and utilized to provide a zeroing function from the distributor and thus permit greater accuracy during distribution. The distributor includes a coded pulse generator that generates pulses in accordance with its movement among the bottles to have in memory an exact indication of where it is located. In that manner, the program may control the location of the outlet of the distributor hose to time the depositing of samples even though different arrangements of bottles may be used in the same container.

The sampler includes a random number generator so that samples will be taken at random times. The pattern is stored in memory. This prevents tampering with sample times by personnel working at a site in which monitoring is taking place. Standard bottles with standard samples may be included so that, if tampering occurs with the sample bottles, it may be detected by interrogating the memory to determine when samples were drawn from the body of water and into which containers they were deposited and which samples or sample bottles should have standard solutions or no solutions in them. Moreover, the software can be drawing and inserting one set of samples in containers according to one program and nonetheless simultaneously follow at least one other program. The other program or programs may be triggered during the first to start program such as by the detection of a programmed pH or flow rate.

From the above description, it can be understood that the pumping system of this invention has several advantages, such as for example: (1) it permits higher average pumping velocities under high head conditions with peristaltic pumps; (2) it provides longer life to peristaltic pump tubes; (3) it increases the life of tubes and reduces lateral movement; (4) it permits more precise positioning of the distributor outlet port; (5) it permits easy attachment of modules for cooperation with the sampler; (6) it permits safe and easy access to the pump tube for replacement thereof; and (7) it provides a security system to avoid tampering with samples.

SUMMARY OF THE DRAWINGS

The above noted and other features of the invention will be better understood from the following detailed description when considered with reference to the accompanying drawings, in which:

FIG. 4 is an exploded perspective view of a liquid sensing device used in the embodiment the invention shown in FIG. 1;

FIG. 5 is an elevational sectional view of a portion of a liquid sensing device used in the embodiment of the invention shown in FIG. 3;

FIG. 7 is a fragmentary simplified perspective view of an embodiment of a sampler broken away to show a distributor and a bottle tub useful in the embodiment of FIG. 2;

FIG. 8 is an exploded fragmentary perspective view of a pump, sensing section and distributor useful in the embodiment of FIG. 2;

FIG. 9 is a fragmentary top elevational view of a portion of the sensing section of FIG. 8;

FIG. 14 is a schematic drawing of an air bubbler module in accordance with the invention;

FIG. 15 is a schematic diagram of the container full detection system;

FIG. 27 is a flow diagram of another portion of the embodiment of FIG. 18;

FIG. 28 is a block diagram of another portion of the sampler of FIG. 2; and FIG. 29 is a block diagram of still another program useful in the embodiment of FIG. 2.

DETAILED DESCRIPTION

Figure 1:
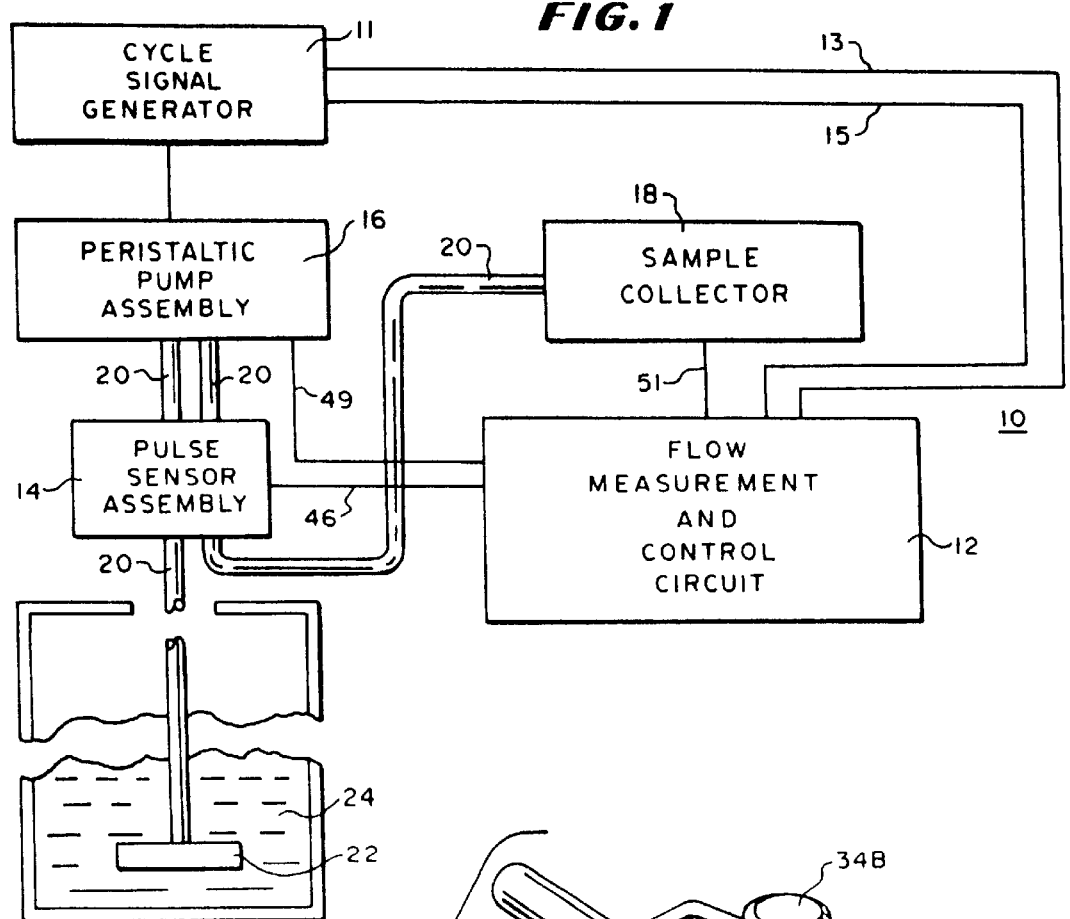
FIG. 1 is a block diagram of a pumping system in accordance with the invention.

In FIG. 1, there is shown a block diagram of a pumping system 10 having a flow measurement and control circuit 12, a pulse sensor assembly 14, a peristaltic pump 16, a cycle signal generator 11 for generating signals indicating the cycles of the pump, a sample collector 18 and a conduit 20. The conduit 20 is fastened to and communicates with an inlet straining device 22 and extends through the pulse sensor assembly 14, the peristaltic pump assembly 16 and the sample collector 18 into which it supplies liquid.

The flow measurement and control circuit 12 is electrically connected to the pulse sensor assembly 14 to receive signals therefrom indicating pumping cycles of liquid after the liquid has reached a specific location and to control the peristaltic pump assembly 16 and sample collector 18 to deposit predetermined volumes of liquid into a sample container or a group of sample containers in accordance with a preprogrammed procedure or under the manual control of an operator.

The cycle signal generator 11 is connected to the rotor of the peristaltic pump in the peristaltic pump assembly 16 and generates a predetermined number of pulses for each cycle. These pulses are transmitted to the flow measurement and control circuit 12 through a conductor 13 to provide an indication of pump cycles and through conductor 15 to indicate the direction of rotation (necessary only in one embodiment) for use in controlling the peristaltic pump assembly 16 in a manner to be described hereinafter.

The conduit 20, inlet strainer 22, peristaltic pump assembly 16 and sample collector 18 may be of any suitable type. A similar arrangement is disclosed in U.S. Pat. No. 4,415,011 except that the sample collecting arrangement of U.S. Pat. No. 4,415,011 utilizes a different type of pulse sensor and relies for control of the volume of liquid on a different circuit arrangement and program. Nonetheless, many different control circuits and different types of pumps which produce pulses when they are pumping, types of sample collector 18, inlet strainer 22 or conduit 20 may be used in the invention.

In use, the inlet strainer 22 is inserted in the liquid 24, samples of which are to be drawn and data such as the amount of fluid for each sample, the time between samples, the size of the conduit 20 and the like are entered through a keyboard. The peristaltic pump assembly 16 is started under the control of the flow measurement and control circuit 12 and begins pumping liquid. As it pumps liquid, there is some force applied to the flexible conduit 20 as the liquid 24 begins to move upwardly through the pulse sensor assembly 14 into the peristaltic pump assembly 16.

The pulse sensor assembly 14 senses pulses, and for this purpose is, in the preferred embodiment, a piezoelectric film contacting the conduit to sense expansion of the conduit. A suitable type of film is available from the Kynar Piezo Film Sensor Division of Pennwalt Corporation having an office at 950 Forage Avenue, Norristown, Pa. 19403. This film is described in a booklet entitled "Piezoelectric Film Sensors An Introduction to the Technology", by Douglas Kehrhahn, available from Pennwalt Corporation, Piezo Film Sensor Division, P.O. Box 799, Valley Forge, Pa. 19482.

Because the pulsations from the peristaltic pump assembly 16 are absorbed by air in the conduit 20 until the liquid reaches the peristaltic pump assembly 16, the pulses received by the pulse sensor assembly 14 do not cross a predetermined amplitude threshold until the liquid reaches a predetermined location. This predetermined location depends on the size of the head and the amount of the liquid being pumped. The greater the head, the closer the predetermined location is to the pump. It is possible to locate the sensor directly at the pump or after (downstream of) the pump and this will change the location of the predetermined point. Data in the lookup table must be adapted to this change in location of the sensor.

With this arrangement, the pulse sensor assembly 14 senses pulse amplitude and determines the interface of pulses and applies the signal to the flow measurement and control circuit 12 indicating that the liquid has reached the predetermined location between the peristaltic pump assembly 16 and the sample collector 18. At this point in time, the flow measurement and control circuit 12 may, in accordance with some standard programs, purge the conduit and redraw the fluid 24, or in others, continue to pump to draw a sample and deposit the sample into a container.

When the location of the fluid 24 reaches the sensor after a purge cycle if there is one, the flow measurement and control circuit 12 causes a predetermined amount of fluid to be deposited in a container within the sample collector 18, and in some embodiments, the sample collector may include a distributor or may move containers to deposit sample in succession during different pumping cycles. The number of pumping cycles required is determined in the preferred embodiment by a computer look-up table containing data based on trial measurements with conduits of the same inner diameter to determine the number of pumping cycles required for a given volume once the interface has been sensed in a manner to be described in greater detail hereinafter.

The statistical database and look-up tables can be calibrated and continuously updated by standard adaptive techniques. More specifically, the amount of sample deposited in containers can be measured and entered into the database to update the look-up table by providing a better average base for the variable parameters.

The sensor may sense some initial bursts of liquid prior to a constant continuous flow. This happens because the sensor detects an initial flow of liquid but in some circumstances, the fluid 24 may contain air bubbles. The fluid measurement and control circuit 12 counts the number of cycles of the pump as indicated by the cycle signal generator 11 for the liquid that flows through a predetermined point and adds those cycles that are significant to the total liquid pumped into a sample container or to a predetermined point required for a rinse or purge cycle. The counting occurs after the liquid interface reaches the predetermined point. This permits the pumping system to more precisely meter liquid into a container.

Figure 2:
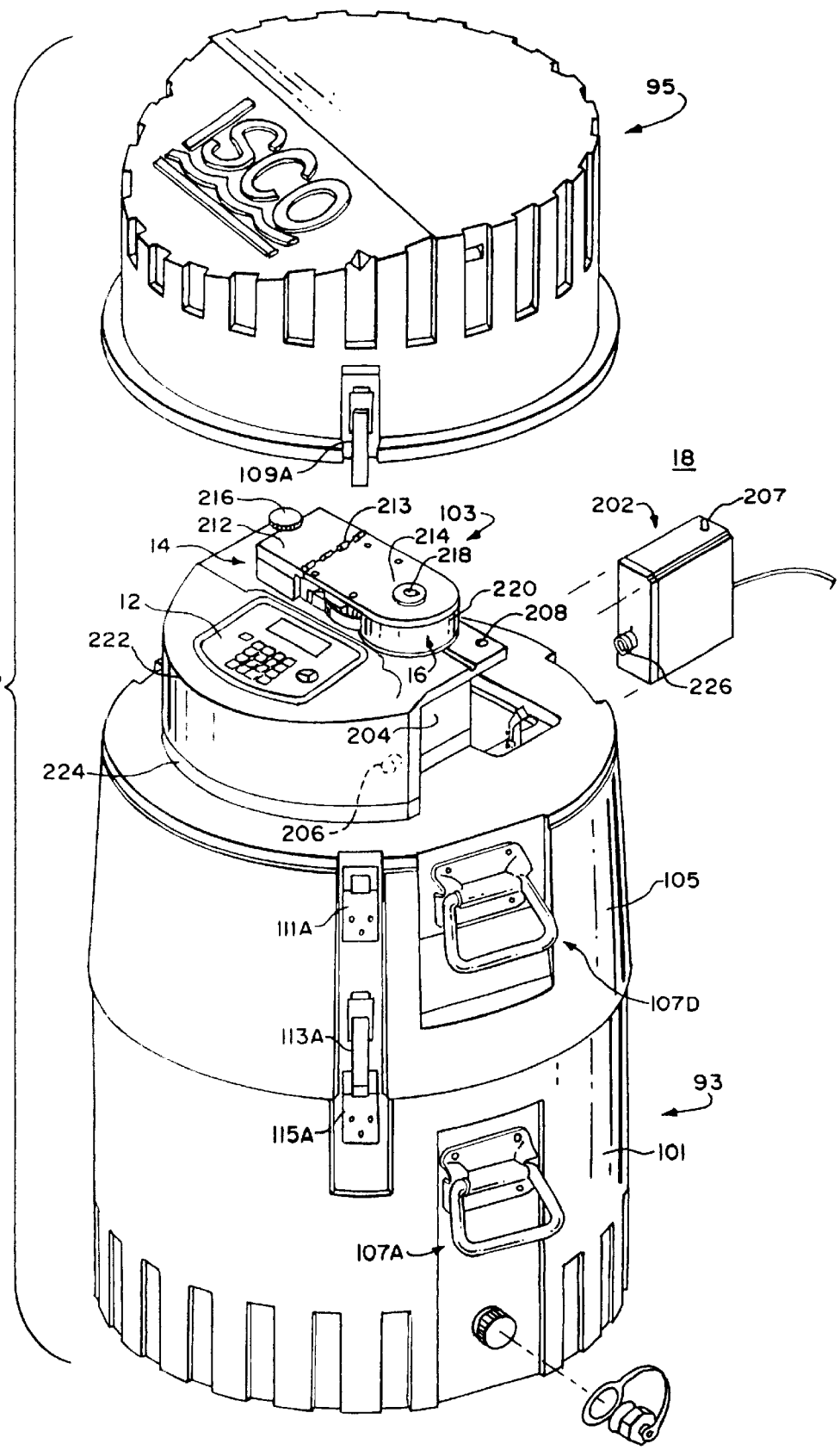
FIG. 2 is an exploded perspective view of a sample collector using the pumping system of FIG. 1 in accordance with an embodiment of the invention.

In FIG. 2, there is shown, in a perspective view, a liquid sample collector 18, having a generally cylindrical base 93 and a generally cylindrical cover 95 fitted to the base 93. The base 93 includes a sample bottle tub 101, a control section 103, and a liquid routing or distributor section 105, conformably fitting between the sample bottle tub 101 and the control section 103, with the distributor section 105 and the sample bottle tub 101 each having three different latch keeper eyelets mounted thereon, two of which are shown at 111A and 115A, adapted to receive the hooks of a latch. The cover 95 and the distributor section 105 each have three different latches mounted thereon, two of which are shown at 109A and 113A, each having eyelets adapted to receive either the hooks of a removable harness by which the sample collector 18 may be suspended in position or may be lowered through a manhole, or a harness by which the sample collector 18 may be secured from being tampered with, or which will accept padlocks for securing the sample collector 18 from being tampered with.

The base 93 and cover 95 are of tough, chemical resistant plastic with external parts that fit tightly together and are latchable in place so that the entire sample collector 18 is able to withstand corrosive environments and even accidental submersion in a liquid for short periods of time.

To latch the cover 95 to the distributor section 105, three stainless steel latches, one of which is shown at 109A, are flexibly mounted at one end to the cover 95 at three circumferentially-spaced locations and each adapted to engage with a corresponding one of three upper latch keeper on the distributor section 105, one of which is shown at a circumferentially-spaced location 111A on the distributor section 105. Preferably the eyelets and latches should be of stainless steel. A drain is provided at the bottom of the base 93 having an externally threaded drain spout 301 that may be closed by the gasket 303 and internally threaded cap 305.

To latch the bottle tub 101 and the liquid routing section 105 together, three lower latches are provided at circumferentially-spaced locations on the distributor section 105, one of which is shown at 113A, and are adapted to engage with corresponding ones of three latching keepers, one of which is shown at 115A, on the bottle tub 101.

The sample collector 18 is used to collect a plurality of samples of a liquid into a group of different containers across a period of time from any body of liquid such as from a river, sewage system, process vat or the like or a single composite sample. Before operation, the containers are loaded into the bottle tub 101, the bottle tub 101, the liquid routing section 105, and the control section 103 are latched together and the cover 95 and control section 103 are latched together.

To operate the sample collector 18, the desired program or programs are inserted into the computer 12, the tubular intake hose 20 (FIG. 1) is inserted into the body of liquid that is to be sampled and the sample collector is started. In operation, liquid is drawn through the tubular intake hose 20 at timed, flow paced or random intervals and routed to one of the different containers within the bottle tub 101 by the liquid routing or distributor section 105. A module 202 such as a pH meter, ultrasonic detector bubbler or the like may be inserted as shown at 204 and connected for cooperation with the sampler before starting as described hereinafter.

The control section 103 includes a sensor assembly 14, a computer 12, a pump assembly 16 and a module section 204 as its principal parts. The sensor assembly 14, computer 12, pump assembly 16 and the module section 204 cooperate together to control the distributor section 105 and the sampler 18. The sensor assembly 14 and pump assembly 16 are housed adjacent to each other near the top of the control section 103. The sensor section 14 is within the hinged cover 212. A thumb screw 216 can be removed to open the cover 212 about the hinge 213 and expose the sensor.

The pump assembly 16 encloses the peristaltic pump rollers and the tube within a metal band 220 and a cover 214. The roller paddle axis of rotation is vertical and an axle ends in the cover 214 at 218 for orbiting of the rollers in a horizontal plane about a vertical axis of rotation. With this arrangement, easy access is provided to the pump for insertion and removal of the pump tubing.

To provide flexibility in operation, the module compartment 204 is adapted to receive a plurality of modules that cooperate with the control section 103. One such module 202 is shown having a connector 226 adapted to engage a complimentary connector 206 in the module compartment 204 for operative connection thereto and having a spring biased detent 207 for engaging a complimentary opening 208 to snap in place.

In the preferred embodiment, four modules are interchangeable in the compartment 204. They are: (1) a four to 20 mA (milliampere) module that provides a connection to receive analogue signals in the range of four to 20 mA range converts to digital signals and transmit them to the computer for storage in the memory of the computer 12; (2) a bubbler that possibly converts to level, or other parameter, provides air to a probe, receives pressure signals, converts them to analogue signals, digitizes them and transmits them to the computer 12 for storage in the computer, after which the computer 12 may determine flow rate and the amount of flow for purposes of triggering sample taking; (3) a pH meter and temperature sensing module that receives signals from a probe indicating temperature and pH, digitizes and transmits them to the computer for storage; and (4) an ultrasonic module that receives depth information from an ultrasonic level measuring probe, digitizes it, and transmits it to the computer for storage in the memory of the computer 12 and possible calculation of flow rate and flow for the purpose of triggering sample taking.

Figure 3:
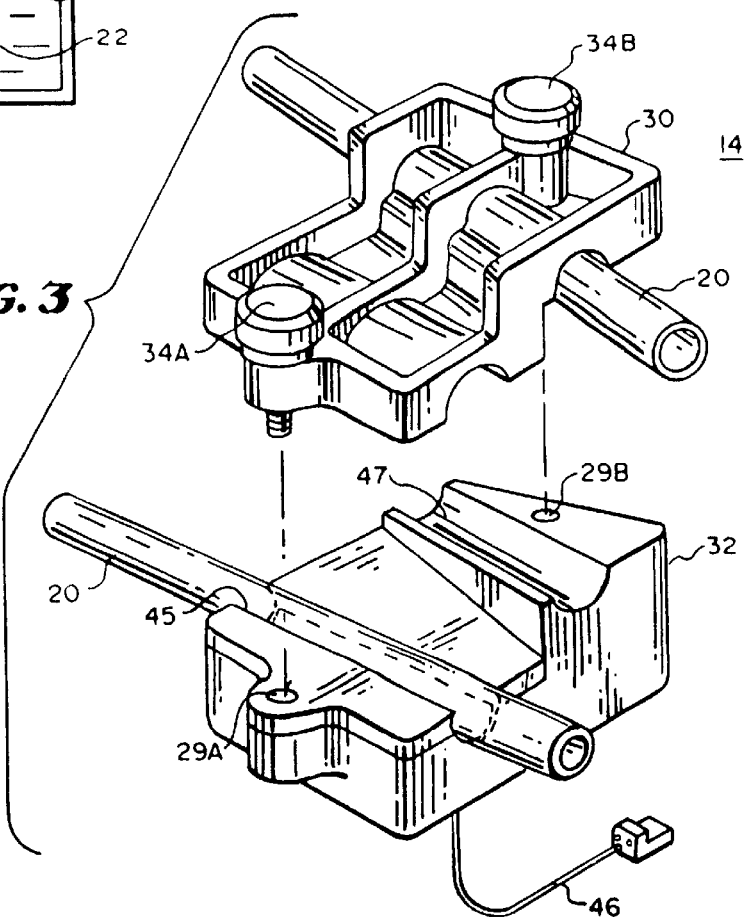
FIG. 3 is a partially exploded, perspective view of a liquid sensing device used in the embodiment of the invention shown in FIG. 1.

In FIG. 3, there is shown a partly exploded perspective view of the pulse sensor assembly 14 having first and second sections 30 and 32. The first and second sections 30 and 32 fit together to form an enclosure having two cylindrical openings extending through it, each of which receive and confine a different part of a length of conduit 20. One part of the length of the conduit 20 fits in a first groove 45 which receives the conduit 20, with a piezoelectric sensor (not shown in FIG. 3) fitting over it to be strained as the conduit 20 deforms. The conduit 20 is looped through the pump and passes in the other direction through a second cylindrical groove. The two sections are held together by fasteners 34A, 34B.

In FIG. 4, there is shown an exploded perspective view of the second section 32 having a housing 35, a piezoelectric sensor 42, a woven fiberglass protective member 37 and first and second seating inserts 38A and 38B. The housing 35 of the second section 32 receives the protective member 37, piezoelectric sensor 42, and inserts 38A and 38B and forms a unit fastened together with first section 30 (FIG. 3) to hold the conduit 20 (FIGS. 1 and 2) against motion caused by the pump 16 (FIG. 1) during its rotation against the conduit 20 and to hold and protect the piezoelectric sensor 42 against the conduit to sense changes in pressure within it caused by action of the pump.

The housing 35 includes: (1) five apertures 33A, 33B, 33C, 33D and 33E sized to receive one end of five fasteners 36A, 36B, 36C, 36D and 36E; (2) four smaller apertures 39A, 39B, 39C and 39D which receive one end of four pins 41A, 41B, 41C and 41D that pass through apertures 43A, 43B, 43C and 43D in the piezoelectric sensor 42, and form a part of the holding means for the sensor 42; (3) cylindrical grooves 45 and 47 and a sensing aperture 47A through which the conductor 46B passes. With this arrangement, the housing 35 aids in holding the sensor 42, the protective member 37 and the inserts 38A and 38B in place. The first section 30 (FIG. 3) and second section 32 of the sensor assembly are held together by thumb screws 34A and 34B (FIG. 3) which engage threaded bores 29A and 29B. The fasteners 36A–36E thread into bosses (not shown) in the inserts 38A and 38B.

The piezoelectric sensor 42 includes: (1) a piezoelectric film 46A which changes its electrical characteristics in response to changes in its strain and generates an electrical potential; and (2) a conductor 46B connected to the film which passes through the second section 32 for electrical connection to the flow measurement and control circuit 12 (FIG. 1) to which it transmits electrical signals indicating changes in the strain in the piezoelectric film 46A. The piezoelectric film 46A includes four apertures 43A–43D passing through it on opposite sides of the groove 45 to form a portion of a holding or clamping means holding the piezoelectric film 46A in place against the conduit 20 (FIGS. 1 and 3).

During installation of the tubing 20 (FIG. 3), the piezoelectric film 46A is pre-stretched by the force of the tubing against the piezoelectric film 46A, the edges of which are held by the pins 41A–41D. The contact between the tubing 20 and the piezoelectric film 46A is maintained intimate by the bias from the stretching of the piezoelectric film 46A and extends over a sufficient surface area with sufficient pressure between the film and the tube 20 to supply adequate coupling for a reliable transfer of force. The coupling is adequate to cause the film to generate repeatable electrical signals in response to a range of forces transferred to it. In the preferred embodiment the area of contact between the piezoelectric film 46A and the tube 20 is ¼ square inch but can be as small as ¹⁄₁₆ square inch.

To protect the piezoelectric sensor 42, a woven fiberglass member 37 with a Teflon (trademark by Du Pont de Nemours, E. I. and Co., Wilmington, Del. 19898 for tetrafluoroethylene fluorocarbon polymers) coating on its top and bottom surfaces and fused over it to form a strong flexible member. It also includes: (1) five apertures aligned with the five apertures 33A, 33B, 33C, 33D and 33E in the housing 35 to receive the two bosses in 38A (not shown) and three bosses in 38B (not shown) that the fasteners 36A, 36B, 36C, 36D and 36E are threaded into; (2) an aperture aligned with the aperture 29A in the housing 35 to hold first section 30 and housing 35 together; and (3) four apertures 45A–45D aligned with the four smaller apertures 39A, 39B, 39C and 39D to receive four pins 41A, 41B, 41C and 41D that are also received by apertures 43A, 43B, 43C and 43D in the piezoelectric film 46A before being seated in the inserts 38A and 38B.

To receive and hold one end of the pins 41A–41D, the inserts 38A and 38B are sized to rest between the protective member 37 and the first section 30 (FIG. 3) and includes: (1) an aperture to receive fastener 34A (FIG. 3) which passes through it and engages threaded bore 29A; and (2) four holes 37A–37D in the side facing the protective member 37 to receive one end of each of the corresponding pins 41A–41D. With this arrangement, the pins 41A–41D hold the film 46A in place on opposite sides of the conduit 20 (FIG. 3) and are in turn held in place by the inserts 38A and 38B on one side and the housing 35 on the other.

In FIG. 5, there is shown an elevational sectional view of the second section 32 taken through lines 5—5 of FIG. 4 and showing the grooves 45 and 47, apertures 29A, 29B, 39B, 39E, 33B, 33C and 33D for seating pins and holding the first and second sections together. As best shown in this view, the conduits and piezoelectric sensor may be securely held in the formed solid rigid housing to receive signals from the pump. Within the groove 45 there is an enlarged portion 45E (FIG. 5) to allow expansion of conduit 20 (FIG. 3) during pulsation. The opening 47A is potted to avoid wire flexing.

In the preferred embodiment, the enlarged portion 45E of the groove 45 is a large enough area to receive the conduit 20 and piezoelectric film 46A (FIG. 4) and forms a recess with a depth approximately 1/16 inch. It is large enough to accommodate expansion of the conduit 20 during pulsation and the depth should be at least the thickness of the film plus one one-thousandth of an inch.

Figure 6:
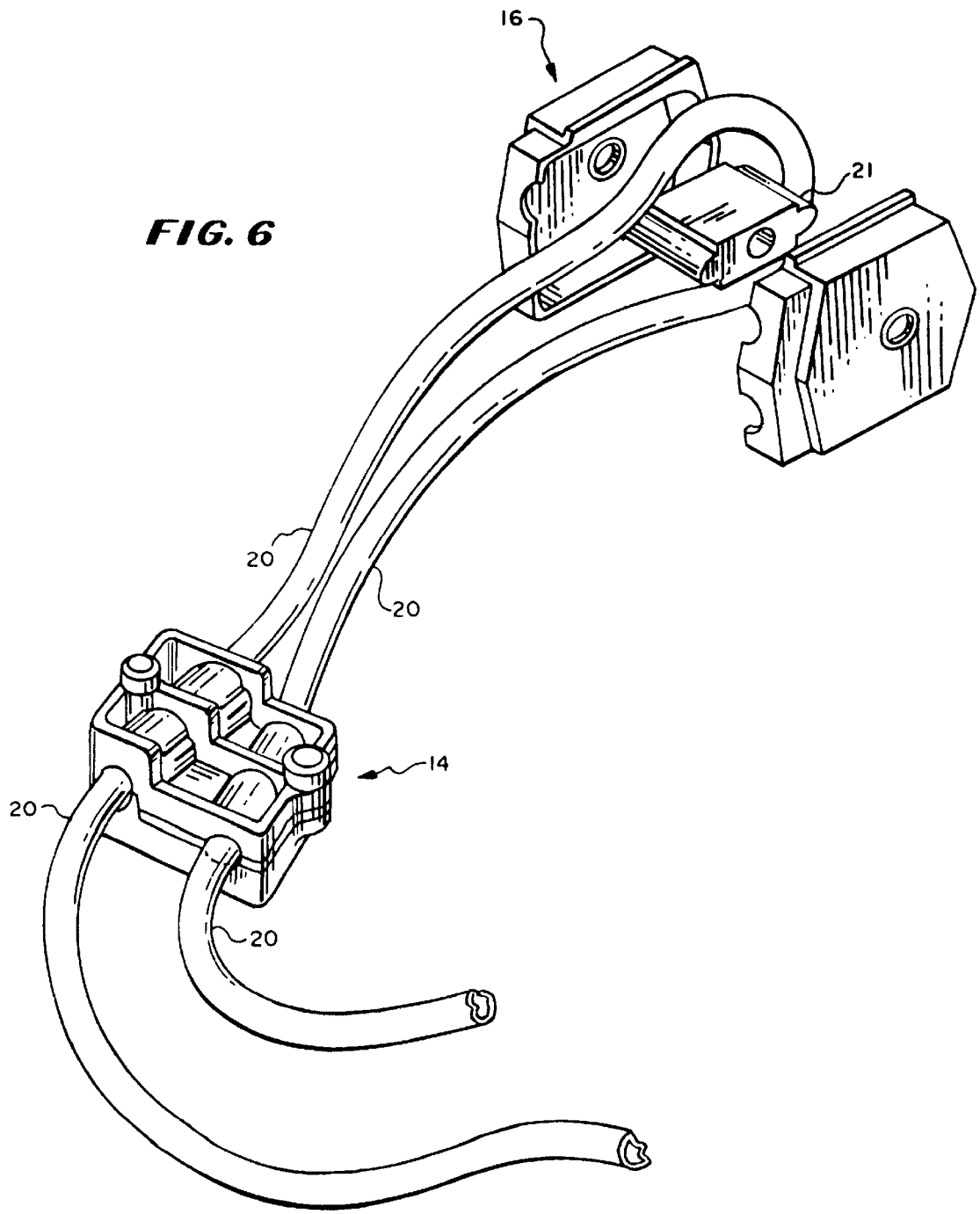
FIG. 6 is a fragmentary, exploded perspective view of the liquid sensing device and pumping system used in the embodiment of the invention shown in FIG. 1.

In FIG. 6, there is shown a simplified view of the peristaltic pump assembly 16 and sensor assembly 14. As shown in this view, the sensor assembly 14 is on the inlet side of the peristaltic pump assembly 16 and in one embodiment spaced therefrom. In the preferred embodiment, the distance between a roller 21 as it contacts tube 20 and the sensor assembly 14 is 3.125 inches and should be less than 18 inches to avoid undue attenuation of the pulses imported through the conduit and liquid from the force of pumps to the sensor assembly 14 before being sensed.

Although the embodiment of FIG. 6 shows a sensing assembly 14 spaced from the rollers 21 of the pump, it is possible to locate a piezoelectric film in the pump housing positioned to sense the relaxation of the conduit 20 between compression by rollers. This results in a change in strain within the piezoelectric film 46A (not shown in FIG. 6). The change in strain has a different time-amplitude characteristic when liquid is in the pump than when it has not yet reached the pump or has passed through the pump.

In FIG. 7, there is shown a simplified perspective view of a sampler 18 broken away to show the interior of the bottle compartment 101 and distributor section 105 having a plurality of sampler containers 260A–260K arranged in a ring, a distributor shaft 230, a distributor support 262 for hose 20 held by a spring 264 and an adjustable hose outlet or nozzle 266 having a downwardly bent nozzle 268 on its end. With this arrangement, the distributor shaft 230 is rotated by a distributor motor from position to position over the containers 260A–260K, which are open in the sampling position, and the pump and distributor deposits samples in them in accordance with a program.

The hose positioner 262 includes a section formed as a split sleeve that permits the section 266 to be inserted under it with the split sleeve 262 being tightened over it and held in place by any of a plurality of thumb screws 270. In this manner, the nozzle 268 may be adjusted for radial length from the distributor shaft 230.

A stop member 272 is fastened upwardly to cooperate with a downwardly extending detent 274. The detent 274 extends downwardly from a base plate and is adapted to engage the stop member 272 for zeroing the distributor.

More specifically, the distributor is moved until it reaches the stop member 274. The pressure against the stop member 274 is sensed by detecting that the arm no longer moves and the motor is reversed until the distributor moves substantially through 360 degrees and engages the stop member 274 again. The travel on both ends of the 360 degree arc is measured and this difference is used to establish a zero point. The zero point is utilized in a manner to be described hereinafter to enable the computer 12 to maintain a record of the position of the distributor at all times. The amount of coasting is recorded and continually averaged at each cycle to more and more closely monitor the position of the distributor arm by repeated averaging so as to continually improve the the performance of the system by reducing the number of "hunt" cycles to correctly obtain the registration of the nozzle outlet of the distributor with the location of the containers.

In FIG. 8 there is shown a fragmentary, perspective, exploded view of the control section 103 and a portion of the distributor section 105 (FIGS. 2 and 7) including the sensor assembly 14 and pump assembly 16 with their respective covers 212 and 214 exploded away and the distributor shaft 230, transmission 232 and optical system 234. As best shown in this view, the distributor shaft 230 and optical system 234 are driven in sychronism by a motor 240 to move the distributor from location to location under the control of the computer 12 (FIG. 2).

To control motion of the distributor, the distributor motor 240 drives a worm 244 on its output shaft. Worm 244 engages gear 246, which turns the optical blocking wheel 250 and worm 248. Optical blocking wheel 250 has opaque portions and light passing protions. The opaque and light passing portions of wheel 250 alternately pass through and interrupt two adjacent light paths to alternately block light and pass light through the paths.

A first light path is between a first light source 252A and a first photosensor 254A and the second light path is between a second light source 252B and a second photosensor 254B. When the wheel 250 rotates in a clockwise direction the first light path is cut just before the second light path and when the wheel 250 rotates in a counter-clockwise direction, the second light path is cut just before the first light path.

With this arrangement, the sequence of pulses from the photosensors to the computer indicates the direction of rotation of the distributor shaft. The phase of pulse pairs with the pulse from the first photosensor 252A just before the pulse from the second photosensor 252B indicates the clockwise angle through which the distributor shaft moves and the phase of pulses with the pulse from the second photosensor 252B just before the pulse from the first photosensor 252A indicates the angle of turning of the distributor shaft in the counter-clockwise direction.

After the distributor system has been zeroed and from counting the number of pulses and the direction, the distributor outlet 268 (FIG. 7) can be moved to any position in the 360 degree circle. The distributor outlet 268 can be moved in either direction.

The pump compartment 16 includes the metal band 220 (FIGS. 2 and 7) having a hinge 300 at one end and a hook encompassing a magnet at the other end 280, with the hinge 300 being connectable at one end of the pump housing 16 and the other end 280 having a keeper over which the hook may be pulled to close the pump. The hook has an opening in it containing a magnet that interacts with a reed switch positioned near the keeper at 282.

With this arrangement, when the magnet 280 is located close to the reed switch indicating the band 220 is closing the pump section, a circuit for pump power is also closable and the pump may run. However, when the band is open, the magnet is removed from the reed switch and the power circuit remains open because the reed switch is not activated by the magnet. This arrangement prevents the motor from operating unless the band is closed. The band may simply be opened by moving the flexible member and unhooking its hooked end to gain access to the pump tube for easy replacement thereof.

Within the pump compartment, is a first raceway 300A for receiving the pump tubing and for cooperation with a complimentary raceway 302 in the top cover 214 to permit the roller to be orbited along the raceway to depress the tubing without crushing it in a manner to be described hereinafter.

In FIG. 9, there is shown an exploded perspective view of another embodiment of second section 32A similar to the second section 32 of FIG. 4 except that one end 43 of the piezoelectric sensor 42A extends downwardly into a slot and is potted in place. Also, the channels for receiving the conduit (not shown in FIG. 9) are relatively level and a Teflon hold-down clip for the fiberglass protective member 37A is shown at 41A to prevent the protective member from moving upwardly as the pump hose 20 (FIGS. 1 and 3) is inserted. The unit functions substantially in the same manner as the sensing unit of which the second section 32 shown in FIG. 4 is a part.

Figure 10:
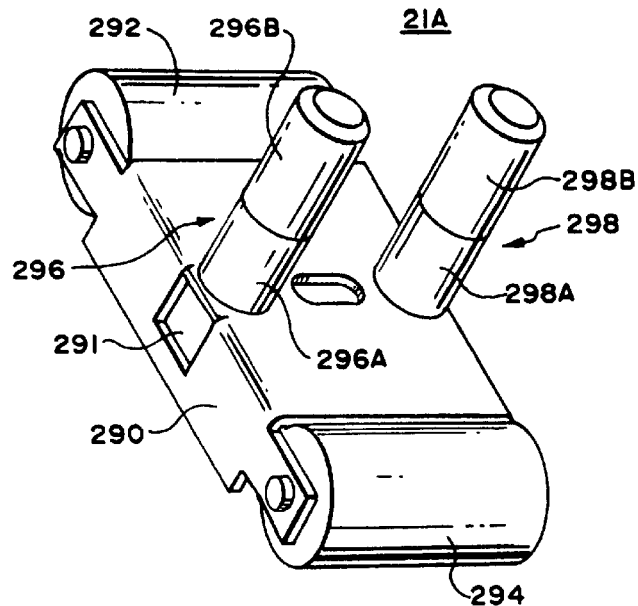
FIG. 10 is a simplified, fragmentary perspective view of a pump roller assembly in accordance with the invention.

In FIG. 10, there is shown an enlarged perspective view of a roller assembly 21A similar to the roller assembly 21 of FIG. 6 having a housing 290, a first end roller 292 on one end of the rotary housing 290 and a second end roller 294 on the other end of the housing, wherein the housing 290 may be rotated about its axis at 291 to orbit the rollers 292 and 294 against the peristaltic pump tube 20 (FIGS. 1 and 3). In this embodiment, two retaining posts 296 and 298 are provided extending perpendicular from the longitudinal plane of the frame 290 and the rotational axis of the rollers 292 and 294. The retaining posts 296 and 298 are adjacent to each other and adapted to straddle the peristaltic pump tube 20 (FIGS. 1 and 3).

The assemblies 296 and 298 are intended to prevent the tube from moving from position to position laterally with respect to the rollers as it stretches from use, and for this purpose, include bottom members 296A and 298A respectively supporting the post 296 and 298 in place and having at their upper end rotary rollers 296B and 298B respectively to rotate with respect to the peristaltic pump tube 20 passing between them.

Figure 11:
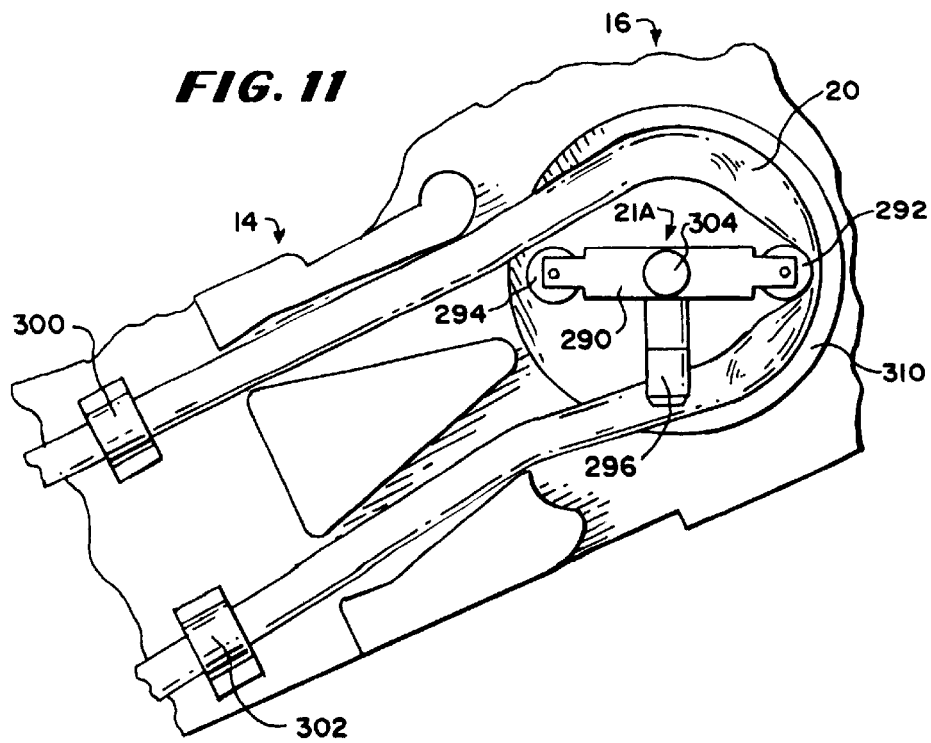
FIG. 11 is a simplified perspective view of an embodiment of pump and sensing system.

In FIG. 11, there is shown a simplified fragmentary plan view of the pump section 16 (FIGS. 7 and 8) and a portion of the sensing section 14 (FIGS. 7 and 8) having the peristaltic tube 20 and an embodiment of roller assembly 21A. The peristaltic tube 20 includes first and second circumferentially extending bands surrounding the tube 300 and 302, slightly elevated beyond the outer wall of the tube, such as for example by 1/16 inch, and approximately ½ inch wide. These raised bands fit conformably within corresponding depressions in the outer surface of the lower member of the sensing unit to enable proper placement of the hose 20 within the pump and sensing unit. It is also possible to use unraised colored bands to aid in the placement of the tube although the indentation and corresponding circumferential bands provide gripping action in addition to ease of placement of the tube.

The roller assembly 21A includes the shaft 304 driven by the pump motor for rotating the rollers 294 and 292 to compress the tube 20 and thus pump fluid upwardly through the sensor. The post 296 is shown on one side of the tube 20 to maintain it in alignment. This post and its companion post on the opposite side of the tube continually rotate about the axis of rotation of the shaft 304 as the rollers are orbited to continually re-align the tube and prevent it from lateral movement.

Figure 12:
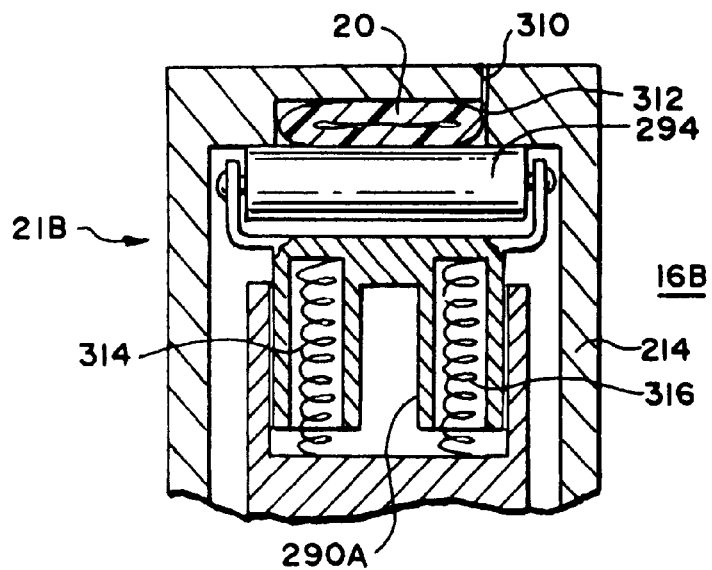
FIGS. 12 and 13 are simplified fragmentary perspective views of two other embodiments of pumping systems.

In FIG. 12, there is shown a fragmentary schematic view of another embodiment of pump chamber 16B having a roller assembly 21B, a peristaltic tube 20, a pump chamber surface 310, a raceway 312 in the pump cover 214, a roller 294 and a roller frame 290A. In this embodiment, the cover 214 closes downwardly so that the raceway 312 engages the edge 310 providing two surfaces spaced so that when the peristaltic pump tube 20 is completely compressed by the roller 294, the side portions of the roller do not rest on the raceway edges. In this embodiment, the roller may be held by a spring biased member in the roller frame 290 but this is not required. The spring rollers allow the tubing walls 20 to be completely compressed but not crushed. The raceway 312 acts as a tube guide to not allow any lateral movement of the tueb 20 within the pump.

Figure 13:
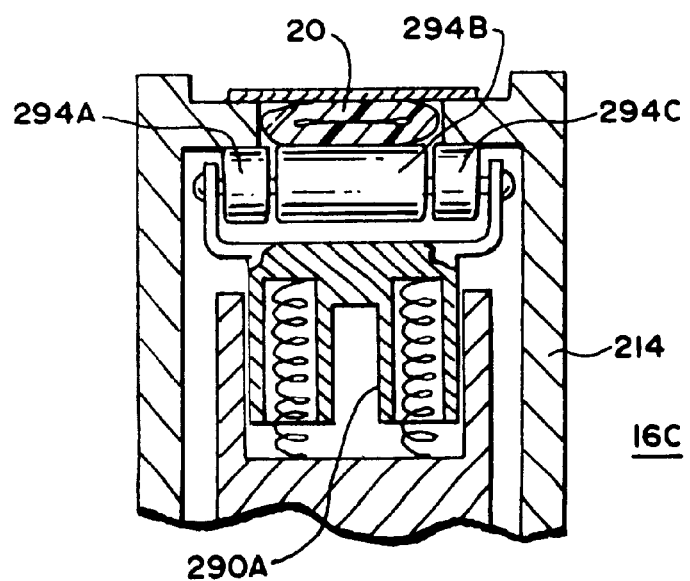

In FIG. 13, there is shown a schematic fragmentary view of another embodiment of pump chamber 16C similar to the pump chamber 16B of FIG. 12 but including a roller formed with three independent roller parts 294A, 294B and 294C. The central roller 294B is sized to fit over the tube 20 whereas the rollers 294A and 294C engage the edges of the cover and base of the chamber so as to not allow roller 294B to crush the walls of the tube 20 but only able to completely compress it. They are all mounted on the same shaft so that the side rollers, which roll independently, hold the roller 294B from crushing the walls of the tube 20.

In FIG. 14, there is shown a schematic diagram of one of the modules 202 (FIG. 2) that cooperates with the control panel 103. This module is a bubbler module shown generally at 202A connected to a desiccant chamber 324, an air inlet 326, a hydrophobic filter 322 and a bubbler line 320. The module 202A fits within the compartment 204 (FIG. 2) in the manner described above and is connected to a bubbler probe through the line 220 to transmit air at a pressure equal to the hydrostatic pressure of the bubbler probe and thus to transmit pressure back to line 320 equal to the hydrostatic pressure to provide an indication of the depth of the probe. The air inlet 326 provides air at a reference atmospheric pressure, which is dried in the desiccant chamber 324 and filtered in the filter 322 before being connected to communicate with the module 202A.

The module 202A includes an air tank 328, a manifold 330, a pump 332, a differential pressure transducer 334, a filter 336, a check valve 338, a bleed oriface or restrictor 340 and a 1.4 psi (pounds per square inch) differential pressure switch 344. The air inlet line communicating with the hydrophobic filter 322 communicates with a second hydrophobic filter 336 to provide an air line into the manifold 330 at substantially atmospheric pressure. This line is also connected to the pump inlet 332, the outlet of which communicates through the check valve 338 to the tank 328 so as to be capable of pumping air into the tank 328 and thus pressurizing it. The check valve 338 prevents back flow through the pump 332.

The 0.004 inch diameter bleed oriface 340 communicates with the air inlet line to the manifold 330, connecting with the filter 336 and the air inlet of the pump 332 within the manifold 330.

Within the manifold, the air inlet line from the bleed oriface 340 also communicates with a line 348 to provide a reference pressure to the differential pressure transducer 334. The bubbler communicates with the differential pressure transducer 334 through the air line 346 from the manifold 330 to transmit a head of pressure to the transducer equal to the depth of the liquid. The bubbler line 320 carrying the hydrostatic pressure communicates with the manifold and with the 1.5 psi differential switch 344 to transmit pressure to both of them. The 1.5 psi differntial pressure switch also communicates with the manifold.

The manifold 330 includes within it a bleeder 350, a three-way valve 356, a normally closed two-way valve 354, and a bubbler oriface 352 which is 0.001 inches in diameter. With this arrangement, within the manifold 330, the bubbler line 320 transmits pressure to the differential pressure switch 344 as does the outlet from the tank 328 so that when the pressure from the outlet of the tank 328 differs from the pressure from the line 322 by 1.5 psi or less than 1.5 psi indicating a low flow rate, the switch 344 energizes the pump to recharge the tank 328. The bleeder oriface 350 permits the escape of air from the manifold at a low rate to conserve power. The two-way valve 354 allows a preprogrammed bypass around the orifice 352 to clear debris from the sensor attached to conduit 320. Air from the air inlet 326 is transmitted through the switch 356 in one position of the three-way valve 356 to apply zero drift pressure to transducer 344 and thus to rezero the electronics. In the other position of the three-way valve, air from the bubbler line 320 at hydrostatic pressure is transmitted to the differential pressure transducer.

In the measuring position, the differential pressure transducer 344 transmits an electrical signal on conductor 360 to a analog to digital convertor at the interface with the computer 12 for development of and the storage of a digital signal indicating the depth of the flow stream being sampled.

Figure 18:
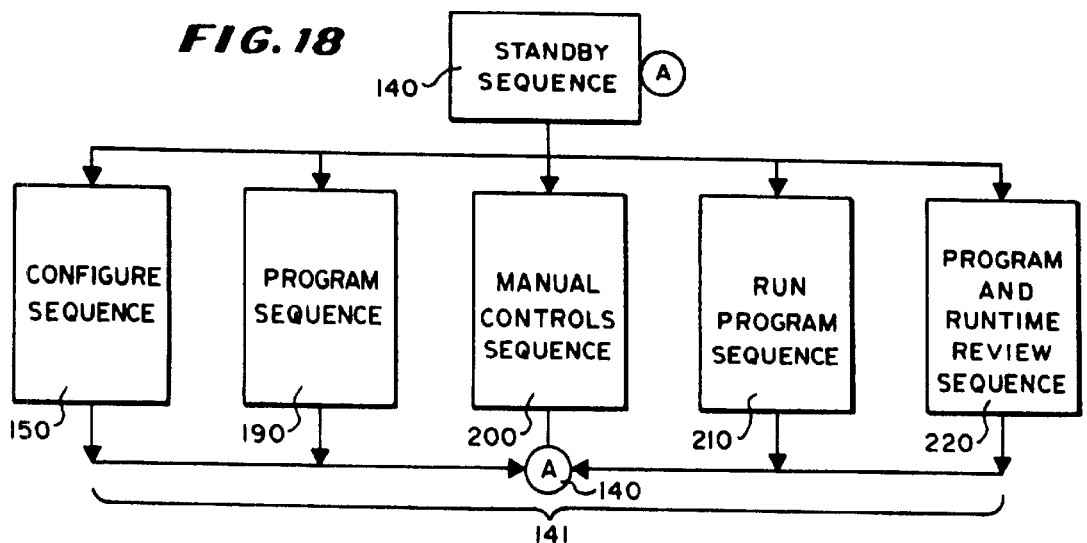
FIG. 18 is a flow diagram of a portion of a prgram used to operate the sampler of FIG. 2.

In FIG. 15, there is shown a schematic diagram illustrating a level detector 403 for a container 400 receiving liquid from a distributor hose 20 within a distributor arm. The container 400 may be one of several containers or a central single container coming directly from the tubing 20 through a central guide without the use of the distributor arm. The container includes a float 402 mounted within a cage 404 fastened to the top of the container. The float 402 includes an upstanding post with a magnet 406 on the top. The magnet 406 may be detected by a reed switch 408 mounted to the top of the bottle tub 93 (FIG. 18).

This arrangement provides three methods of detecting overflow of a container. The first method is by the float 402 rising within the cage 404 as the liquid rises near the outlet of the container 400 until it is in proximity with the reed switch 408. The activation of the reed switch provides a signal indicating a near over flow condition. In an alternative embodiment, the mouth of the conduit 20 is adjacent to the container opening. When the liquid rises above the outlet from the conduit 20, a purging cycle which would normally pump air out of the tube in a direction away from the container, pulls liquid from the container, thus causing transmission of pulses from the pump during purge operations. These pulses are counted, then compared with a recent history of purge counts threshold, to detect an over-flow condition. A third method is to sense the increased pulses when the drawn liquid moves a sufficient distance toward the peristaltic pump In drawing samples from a stream for depositing into sample containers, it is desirable that water be sampled or pulled from the stream at a rate of two feet per second which is the typical speed of liquid in a sewer. However, it is difficult to do this under a relatively long head of pressure with a peristaltic pump because of the inability of the pump to draw liquid at that rate. This difficulty occurs because, as the speed of the peristaltic pump is increased under a high head of pressure, the tube fails to return to its fully expanded position after a roller compresses it. This limits the amount of force pulling the liquid upwardly because the tube does not expand its complete distance.

In the specification, the terms "coefficient of restoration" and "energy of restoration" are utilized to describe the ability of the tube to return to its fully restored position. Energy of restoration is the amount of energy which can be stored by the tube at a given speed of the pump or of liquid being draw through the tube. The coefficient of restoration is the fraction of the distance returned by the tube after compression at a particular speed and head of pressure. Thus a coefficient of restoration of one indicates that the tube is fully restored.

The energy of restoration is a function of the wall thickness of the tube, the modulus of elasticity of the material in the tube and the speed of compression or the time period between compressions.

To be able to draw liquid at a rate of two feet per second under a minimum head of 20 feet, a silicon tube designated MDF-0215 available from Dow Corning Corporation, Midland, Mich. 48686-0994 with a wall thickness of 0.145 inches with an internal diameter of 0.375 inches and a post cure with a sufficient restoration of one at 300 rpm (revolutions per minute) is used. This combination can pull liquid against a head of 23 feet at a rate of two feet per second. Generally, different materials and thickness may be selected by trial and error to obtain a restoration factor of one at the desired rpm, head of pressure and rate of drawing the liquid, which has as a standard two feet per second. Post curing means curing at a slightly elevated temperature until the desired modulus of elasticity is obtained to provide the desired restoration coefficient. The modules of elasticity is stable at this point and will not change by more than ten percent.

Figure 16:
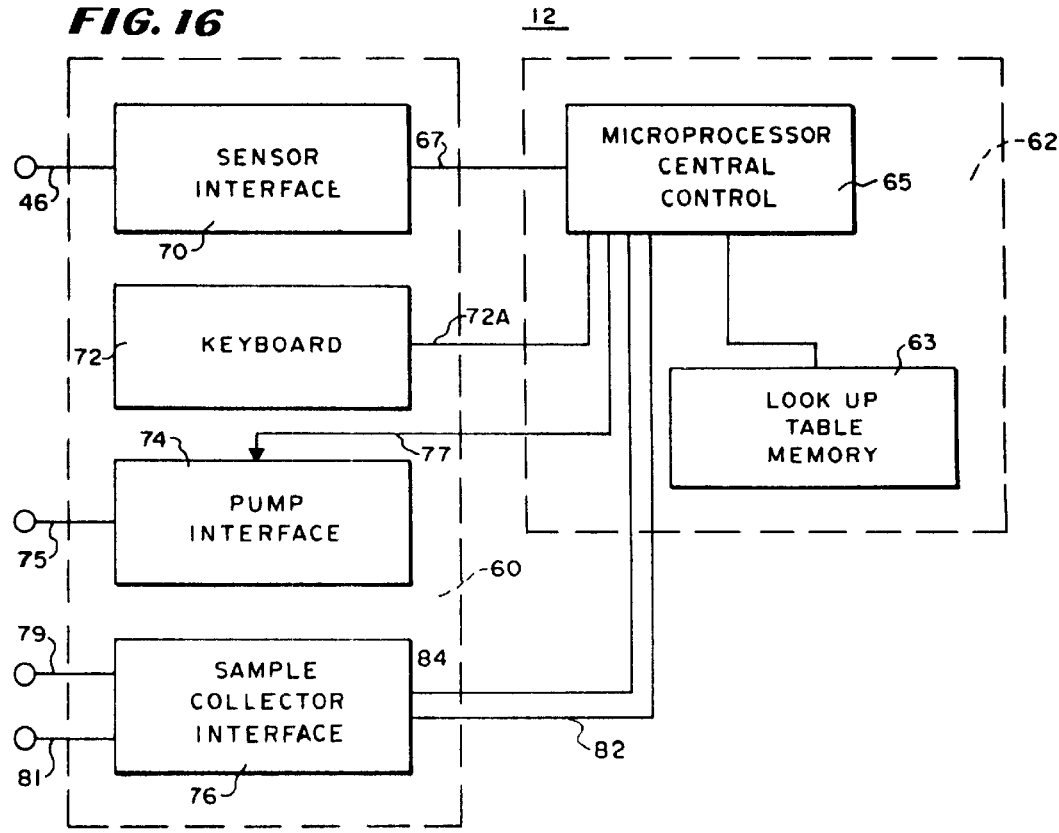
FIG. 16 is a block diagram of a portion of the pumping system of FIG. 1.

In FIG. 16, there is shown a block diagram of the flow measurement and control circuit 12 having a microprocessor 62 and an interface assembly shown generally at 60. In the preferred embodiment, the microprocessor 62 is a Model Z8S180 sold by Zilog and includes a look-up table memory 63 as well as the normal logic components 65 forming the microprocessor central control. The look-up table memory 63 is accessed by the central control to look-up values corresponding to certain numbers of cycles of the pump 16 (FIG. 1) applied to it through the pump interface 60 through a conductor 77.

The interface 60 includes a sensor interface 70, connected to the pulse sensor assembly 14 (FIG. 1) through a conductor 46 and to the microprocessor 62 through a conductor 67, a keyboard 72 for entering data into the microprocessor 62 through a cable 72A, a pump interface 74 for transmitting start and stop signals through a cable 75 to the peristaltic pump assembly 16 (FIG. 1) in response to signals from the microprocessor 62 through a conductor 77 and a sample collector interface 76 receiving signals from the sample collector 18 (FIG. 1) on a conductor 79 and transmitting signals to the sample collector 18 through a conductor 81. The sample collector interface 76 transmit signals to the microprocessor 62 through a conductor 82 and receives signals through a conductor 84.

With this arrangement, the microprocessor receives indications of cycling of the peristaltic pump assembly 16 when the water interface reaches a predetermined location, counts those cycles and uses the count for other control functions such as moving bottles in the sample collector, stopping and reversing the pump and restarting the pump for another cycle, starting timing for the intervals between drawing samples and the like.

In the preferred embodiment, once the pumping system has determined that liquid is flowing from the amplitude of measured pulses, sensed cycles of the pump are counted during the time the amplitude of the strain pulses is above the threshold.

Figure 17:
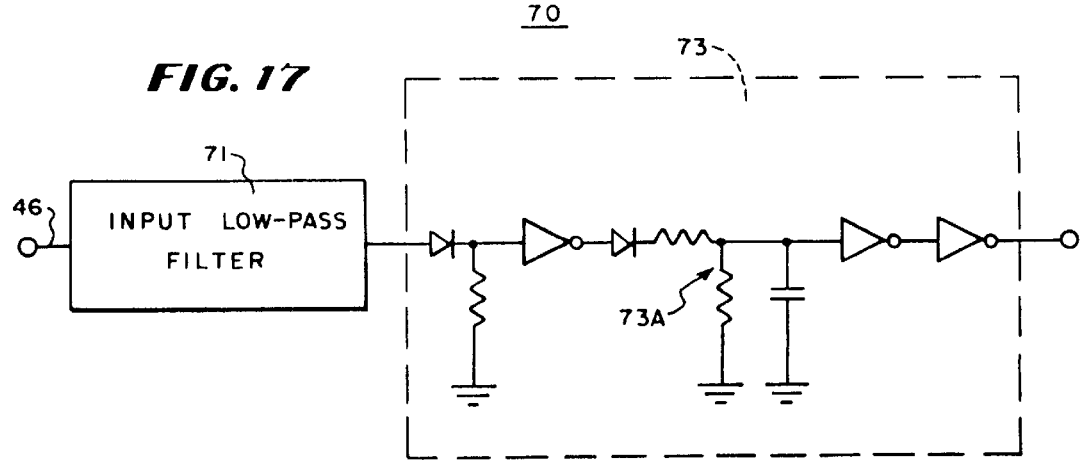
FIG. 17 is a block diagram of a portion of one of the embodiment of FIG. 16.

In FIG. 17, there is shown a block diagram of the sensor interface 70 having an input low-pass filter and pulse shaping section 71 and an output section 73. The input low-pass filter 71 is a National MF6 set to have a 45 hertz cut-off and a 0.5 volt threshold. The output section 73 shapes the input pulses to a square wave and discriminates against pulses having a time duration less than a predetermined time set by the RC circuit 73A. However, any suitable interface may be used.

In FIG. 18, there is shown a block diagram of the main subprograms of the program that controls the pumping system 10 (FIG. 1) including a standby mode subprogram 140 and a plurality of operating subprograms showns generally at 141. When the pumping system 10 is turned on and after completion of each of the operating subprograms shown collectively at 141, the program automatically goes to the standby mode 140. The user then enters the command to go to any of the other subprograms of the pumping system 10 (FIG. 1). The main subprograms shown in the group 141 include: (1) configure sequence 150; (2) program sequence 190; (3) manual controls 200; (4) run program 210; and (5) program and runtime review 220. Many programs used in the operation of a pumping system are not related to the invention and are standard for equipment of this type. These programs are not described in any detail herein. However, the programs related to the invention are described in flow diagram form.

Before starting the pump, the user may enter data to set up the pumping system 10 (FIG. 1) so that it will operate to the user's specific needs. If the user does not wish to change the settings from the most recent run, then he would not use these programs. This user-defined information may be entered in the configure sequence 150 and the program sequence 190. The configure sequence 150 is used to enter certain data such as bottle count and size, correct time and suction line information. Most of the data entered in the configure sequence 150 are of a type that do not change often. The program sequence 190 is used to enter data for the specifics of the sampling routine such as sample volume, frequency and distribution method.

The run program sequence 210 runs the sampling routine using the data programmed in the configure sequence 150 and program sequence 190 and the program and runtime review 220 displays the program settings and sampling routine results. The manual controls program sequence 200 sequences through steps that operate the pump and distributor in response to manually entered instructions by the operator.

Figure 19:
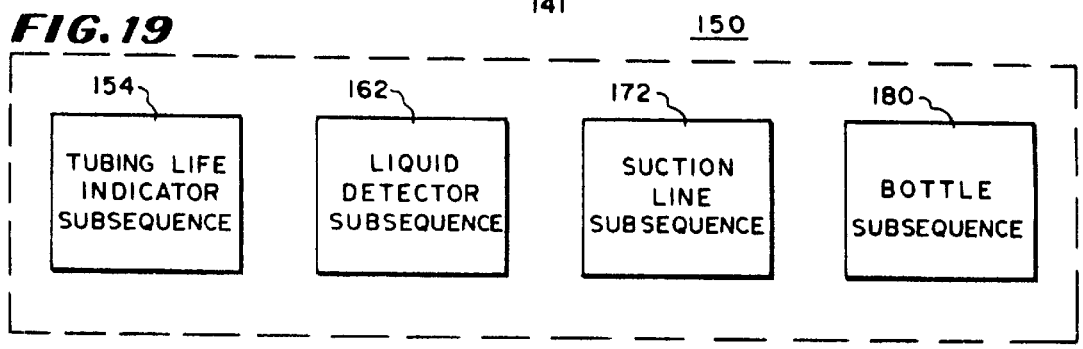
FIG. 19 is a flow diagram of a portion of the embodiment of FIG. 18.

In FIG. 19, there is shown a block diagram of the main parts of the configure sequence 150 (FIG. 18). The parts include: (1) tubing life indicator subsequence 154; (2) liquid detector subsequence 162; (3) suction line subsequence 172; and (4) bottle subsequence 180. The subsequences together provide data points into the system for configuring the pumping system 10 (FIG. 1).

Figure 20:
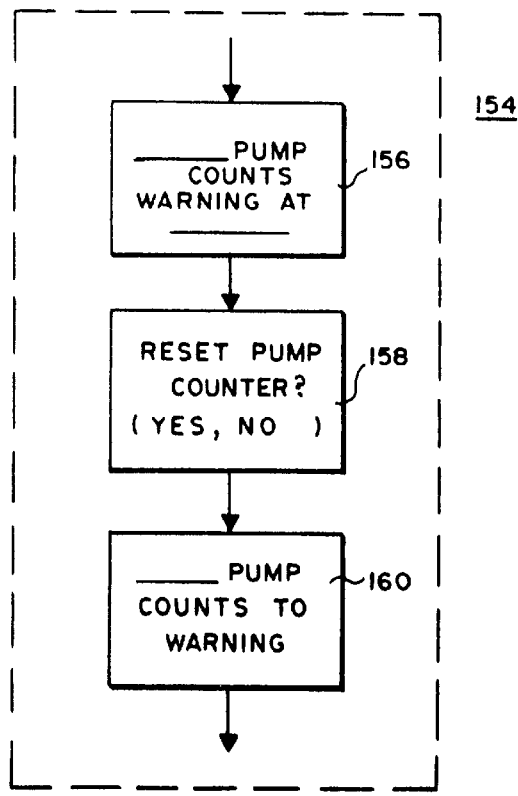
FIG. 20 is a flow diagram of still another portion of the embodiment of FIG. 18.

In FIG. 20, there is shown a flow diagram of the tubing life indicator subsequence 154 (FIG. 19) of the configure sequence 150 (FIGS. 18 and 19). The tubing life indicator subsequence 154 monitors usage of the tubing 20 by keeping track of how many cycles the pump has made against the tubing 20 in any direction since its last replacement and warns the user that the tubing 20 should be replaced. Included in the tubing life indicator subsequence 154 are: (1) a pump counter subsequence at 156; (2) a reset pump counter subsequence at 158; and (3) a warning trip point subsequence at 160.

The total pump strokes (12 for each revolution of the pump) and the point at which the counter warns the user that it is time to change the tubing 20 are displayed to the user at 156. The range of pump counts for the life of the tubing 20 is usually between 50,000 and 2 million pump counts. If the tubing 20 has been replaced, the user would indicate yes in the reset pump counter subsequence 158 to reset the pump counter subsequence 156. The user-defined warning trip point is entered in subsequence 160. While the pump is pumping, the total pump counts are updated in a counter and compared to the user-defined count. When the update count exceeds the user-defined count, a warning is given.

Figure 21:
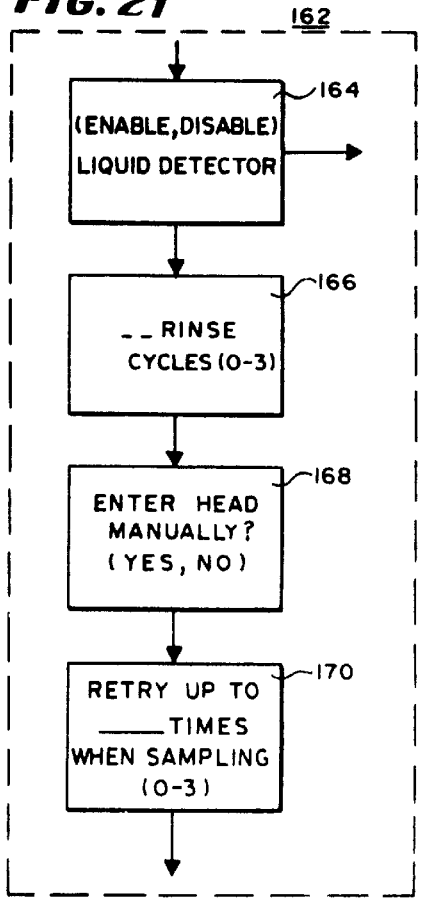
FIG. 21 is a block diagram of still another portion of the embodiment of FIG. 18.

In FIG. 21, there is shown a flow diagram of the options for the liquid detector subsequence 162 (FIG. 19) of the configure sequence 150 (FIGS. 18 and 19). The liquid detector subsequence 162 controls the liquid detector and related settings and how many times it will be used to detect liquid. The options for the liquid detector subsequence 162 include: (1) a rinse cycle subsequence 166; (2) a manual head subsequence 168; and (3) a retry subsequence 170.

The head is entered in the programming sequence 190 (FIG. 18) or determined by the number of pump counts to liquid.

To detect the liquid either in the rinse cycle or during collection of the sample, then the program requests the user to specify: (1) the number of rinse cycles in the rinse subsequence 166; (2) whether a head will be entered manually in the manual head subsequence 168; and (3) the amount of retries in the retry subsequence 170. The retry subsequence 170 controls the amount of retries for both the rinse cycles and the actual collection of sample if no liquid is detected during either process.

Figure 22:
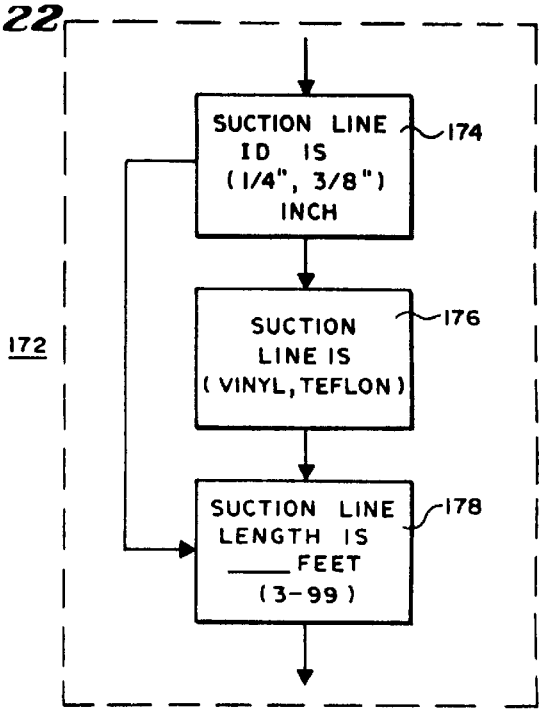
FIG. 22 is a block diagram of another portion of the program of FIG. 18.

In FIG. 22, there is shown a flow diagram of the suction line subsequence 172 (FIG. 19) of the configure sequence 150 (FIGS. 18 and 19). The suction line subsequence 172 is used gather information concerning the suction line, generates the look-up tables and sets the number of post-purge counts. The subsequences in this program are: (1) the inner diameter subsequence 174; (2) the material subsequence 176; and (3) the length subsequence 178.

In the preferred embodiment, the inner diameter of the suction line entered in the subsequence 174 is entered in inches such as one-quarter inch or three-eighths of an inch, the choice of suction line entered in the material subsequence 176 is either vinyl or Teflon and the length of the suction line entered in the length subsequence 178 can be between three and ninety-nine feet.

Figure 23:
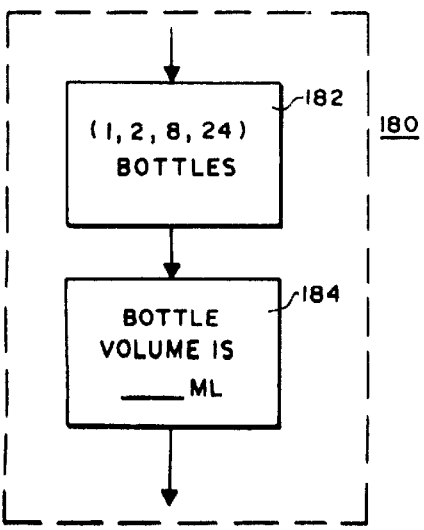
FIG. 23 is a flow diagram of a portion of still another embodiment the program of FIG. 18.

In FIG. 23, there is shown a flow diagram of the bottle subsequence 180 (FIG. 19) of the configure sequence 150 (FIGS. 18 and 19). The bottle subsequence 180 is used to set maximum sampling volumes and provide information to the distributor movement routine.

Two of the subsequences included in the bottle subsequence 180 are bottle number subsequence 182 and bottle volume subsequence 184. The bottle number subsequence 180 is used to enter the amount of bottles in the base and the bottle volume subsequence 184 is used to enter the maximum volume of liquid to be inserted into each bottle.

Figure 24:
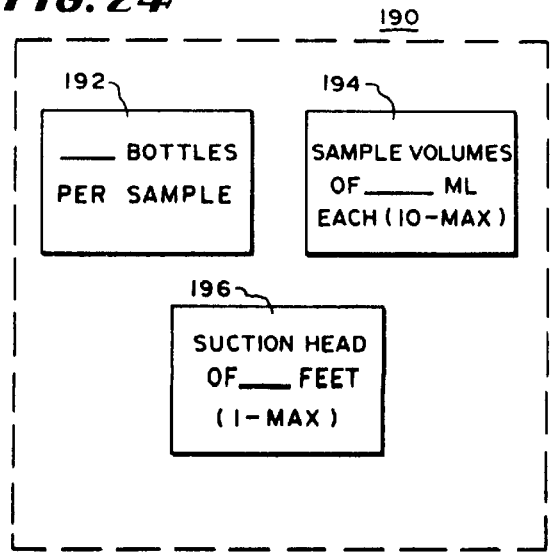
FIG. 24 is a flow diagram of a portion of the program segment of FIG. 18.

In FIG. 24, there is shown a flow diagram of portions of the program sequence 190 (FIG. 18). The program sequence 190 is for entering specifics of a sampling routine which include: (1) the bottles per sample subsequence 192; (2) the sample volume subsequence 194; and (3) the head subsequence at 196. The number of bottles per sample is entered in the sample subsequence 192 and the amount of sample to be distributed into each bottle is entered in the sample volume subsequence 194.

To ensure a more accurate calculation of the pump count maximum, the suction head is entered in the head subsequence 196. The suction head is used to supply information supporting the program operation in the liquid detector subsequence 162 or the user indicated in the head subsequence 168 that a head would be manually entered (FIG. 21). In the preferred embodiment, the user can enter a minimum volume of sample of 10 milliliters and a minimum suction head of one foot.

Figure 25:
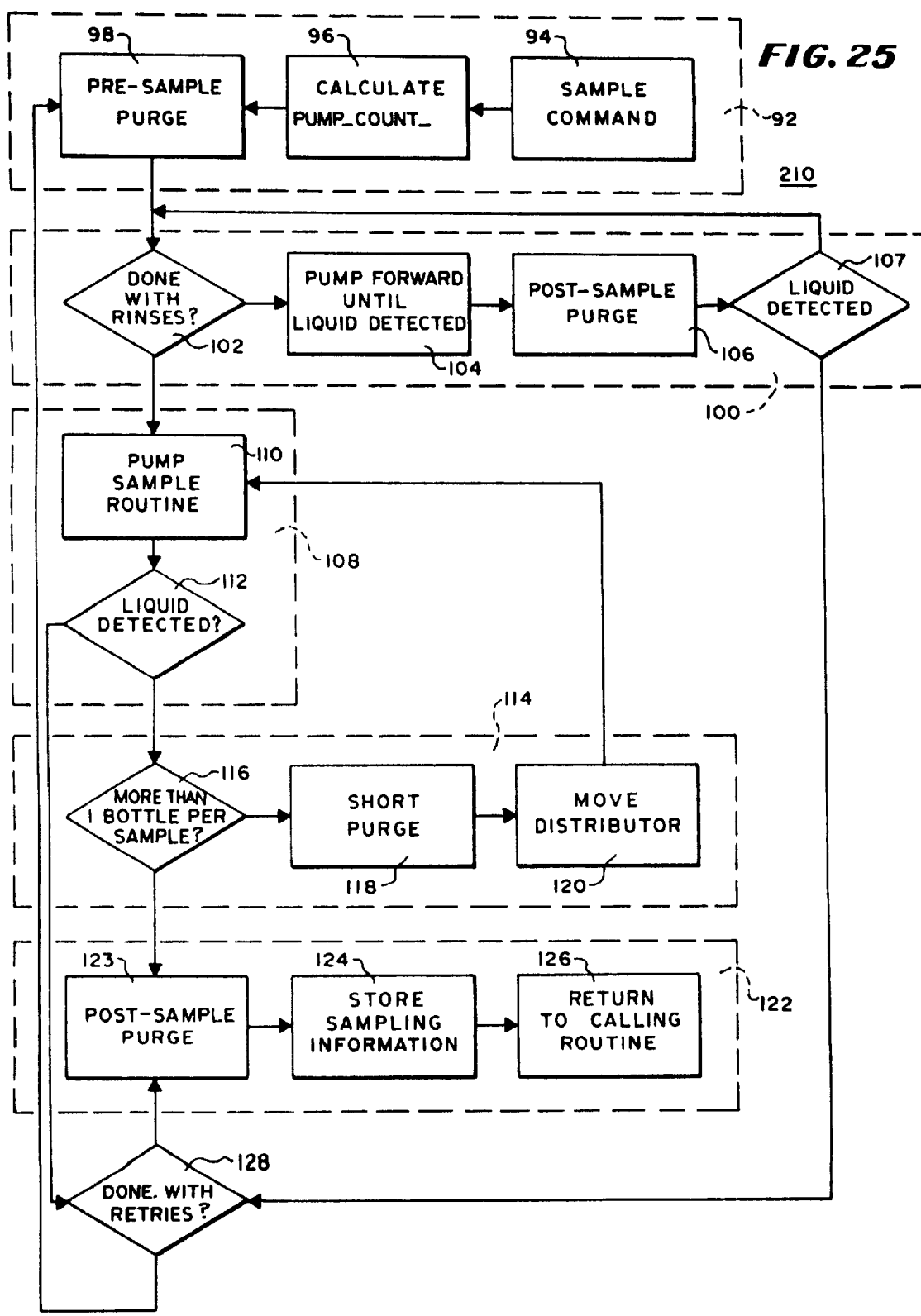
FIG. 25 is a block diagram of still another portion of the embodiment of FIG. 8.

In FIG. 25, there is shown a flow diagram of a portion of the run program sequence 210 for drawing and distributing a sample in accordance with an embodiment of the invention. The run program sequence 210 includes: (1) the series of steps 92 relating to starting the pump; (2) the rinse routine 100; (3) the series of steps 108 relating to drawing a sample; (4) the series of steps 114 relating to distributing the sample; (5) the series of steps 122 relating to storage of the sampling information; and (6) the step 128 of retrying a rinse routine or pump sample routine.

The series of steps 92 relating to starting the pump include the step 94 of receiving the sample command, the step 96 of calculating the maximum pump count and the pre-sample purge step 98. After the sample command 94 has been received, a maximum pump count is calculated based on the head entered in the head subsequence 196 (FIG. 24) or the head from the previous sample if no head was entered. Only one value for the head is used to calculate the maximum pump counts and is used throughout the program segment. The pre-sample purge command 98 is then performed to clear the strainer of any debris which may have collected since the last sample was taken.

After the pre-sample purge is completed, the rinse routine 100 is activated which includes the step 102 to determine if a rinse should be performed or if a second or third rinse should occur. Rinse routines have already been preprogrammed by the user in the rinse subsequence 166 (FIG. 21). If a rinse is programmed, the liquid is pumped forward in the step 104 until a predetermined amount of liquid is detected in step 107 and the liquid is purged in the step 106.

If the predetermined amount of rinse liquid is detected as having reached its destination, the rinse routine 100 is begun again as indicated at 102. If another rinse routine is remaining, the liquid is pumped forward at 104 and the remaining steps of the rinse routine are carried out. The rinse routine 100 is repeated until there are no further rinses. When the rinses are complete, the series of steps 108 relating to drawing a sample continues with the pump sample routine 110 and the step 112 of detecting the liquid.

If no liquid was detected during the rinse routine 100 in the step 107 or the step 112 of the series of steps 108, the program in the step 128 accesses the retry subsequence 170 of the liquid detector subsequence 162 (FIG. 11) to find out if it should retry pumping sample before shutting down. If the user entered any retries, and the total amount of retries has not been met, the program returns to the pre-sample purge 98 and starts the rinse routine 100.

If all of the retries have been made or if no retries were programmed, the controller performs a post sample purge at 123, stores the sampling information at 124 and returns to the calling routine at 126 of the steps 122.

If a rinse routine 100 was not programmed, the steps 104, 106 and 107 are skipped and the program goes directly to drawing a sample at 110 and determines if liquid is detected at 112. The pump sample routine 110 is the actual process of drawing and measuring the sample and will be later described in more detail.

When it is indicated at 112 that liquid was detected, the series of steps 114 relating to distributing a sample is performed. The first step of the series of steps 114 is the step 116 of determining if sample is to be inputted into one or more bottles. If only one bottle will be filled, a user-defined amount of sample is then emptied into the bottle, a post sample purge is performed at 123, the sampling information is stored at 124, and the program returns to the calling routine at 126 in the series of steps 122.

If there is more than one bottle to be filled, a short purge 118 is made to back the liquid up so that it can detect a second user-defined amount of sample and the the distributor is moved to the next sample bottle at 120.

The program segment 210 then returns to the pump sample routine 110 until data is received at 112 that the user-defined amount of liquid is detected. The program checks whether there is more than one bottle left to fill at 116 and then empties the sample into a sample bottle. If more sample is needed, the remaining steps, 118 of purging the sample and 120 of moving the distributor to the next bottle are repeated again. The steps of emptying the sample into the bottle at 116, purging the liquid at 118 and moving the distributor at 120 are repeated until it is indicated at 116 that no more sample will be distributed. When no more sample is needed, a post sample purge is performed at 123, the sampling information is stored at 124, and the program returns to the calling routine at 126 in the series of steps 122.

Figure 26:
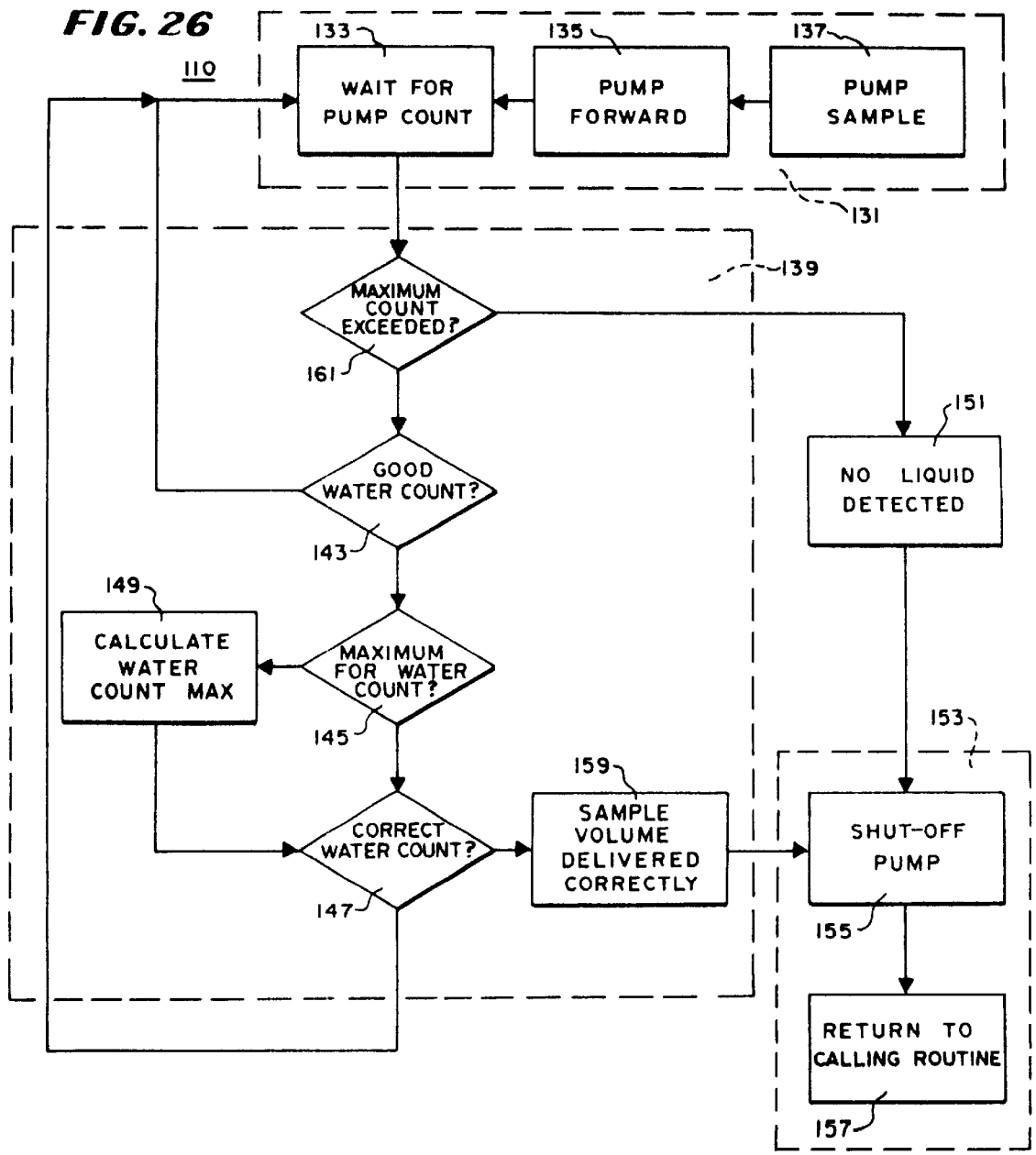
FIG. 26 is a block diagram of another embodiment of FIG. 18.

In FIG. 26, there is shown a flow diagram of the pump sample routine 110 of the program segment 210 (FIG. 25) for drawing and distributing a sample. This routine is the actual pumping of the sample to collect a predetermined amount of liquid in a sample bottle. The pump sample routine 110 includes: (1) the series of steps 131 relating to the beginning stages of pumping; (2) the series of steps 139 related to obtaining the water count; (3) the step 151 of saving information that no liquid was detected; and (4) the series of steps 153 of stopping the pump.

In the series of steps 131, a pump sample command is received at 137 and the sample is pumped upstream through the tube 20 (FIGS. 1, 3 and 6). The sample is then continually pumped and the program waits for a pump count change at 133. The maximum pump count was predetermined based on the head of the previous sample or measured by the user and entered into the program before the user began the pump (not shown) in the configure sequence 150 (FIG. 18).

The program 110 then goes through a series of steps at 139 starting with determining if the maximum pump count has been exceeded in the step 161. If the maximum pump count has been exceeded, the program will save the information indicating that no liquid was detected at 151 and proceed to the series of steps 153 of stopping the pump. During shutdown of the pump, the program shuts the pump off at 155 and returns to the calling routine at 157.

If the maximum pump count has not been exceeded at 161, it is then determined whether a good water count was found at 143. The program determines if a water count is received so near to the beginning of a sample drawing run as to indicate an error. This can occur in the first few cycles such as for example four cycles of the pump. After a predetermined number of cycles of the pump, this type of error tends not to occur. In the preferred embodiment, the pump must have counted at least 50 counts before the count is considered good. If it was not a good water count, the program: (1) returns to waiting for the pump count at 133; and (2) maintains in memory the amount of water counts already received and adds a new water count to the previously received water counts.

If it was a good water count, it is then determined if a new maximum amount of water counts should be calculated at 145. If a new maximum should be made, the program calculates a new maximum water count at 149, using the head from the previous sample or the head defined by the user in the head subsequence 196 (FIG. 24), and then decides at 147 if the sample water count is the correct amount. If not enough sample was pumped, the program returns to the wait for the pump count at 133 and pumps more liquid until it has pumped a predetermined amount of pump counts and continues with the series of steps 139 starting at 161 to determine if the maximum count was exceeded. If the pump did receive a correct water count, it is recorded in memory at 159 that the sample volume was delivered correctly and proceeds with the series of steps 153 of shutting down the pump at 155 and returning to the calling routine at 157.

If it is not necessary to calculate the maximum water count, then the program skips the step 149 and determines at this point if it is a correct water count at 147, records that the sample volume was delivered correctly at 159 and proceeds with the series of steps 153 of shutting off the pump at 155 and returning to the calling routines at 157.

When the program returns to the calling routine at 157, the memory is accessed to find out if the liquid was detected at 112 (FIG. 25) and if it was not, the program would advance to the program at 128 to access 170 of the options for the liquid detector control 162 (FIG. 19) of the configure sequence 150 to find out if it should retry pumping sample before shutting down. If the user entered any retries, and the total amount of retries has not been met, then the program returns to purging the pre-sample at 98 and continuing with the rinse routine 100 (FIG. 25).

In FIG. 27, there is shown a flow diagram of the program and run review sequence 221 (FIG. 18). The program and run review sequence 221 is used to check program setting or sampling routine results. The subsequences included are the pump tubing warning subsequence 225 and the sample information for the last sample routine subsequence 223.

Each time the pump count maximum for replacing the tubing is exceeded, the pump tubing warning message at 225 is displayed. The threshold for the pump count maximum has been user-defined in the tubing life indicator control 154 at 156 (FIG. 20) before beginning the pump. If the user does not enter a new threshold, the threshold from the previous sampling process will be used.

After each sample gathering process, certain information is stored in memory for future use at 223. Included are: (1) if the sample process was performed and no liquid was detected at 227; (2) the time and date at 229; and (3) the number of pump counts before liquid was detected at 231 and the amount of time for the entire pump cycle. The number of counts before liquid was detected at 231 is used to calculate the head at 149 (FIG. 26).

In FIG. 28, there is shown a block diagram of another embodiment of tubing life indicator circuit 154A for providing a signal after a predetermined number of strokes of roller against the tube 20 (FIGS. 1, 3 and 6) in the peristaltic pump assembly 16 (FIG. 1), having the cycle signal generator 11, a counter 241, a switch 247, a manually resettable switch 243 and a warning light 253. The counter 241 is directly connected to the conductor 13 to receive all counts regardless of direction and having an output set at a predetermined number of counts connected to the resettable switch 243 to actuate the switch at the predetermined number of counts and thus energize the warning light to which it is connected.

With this arrangement, the operator may set the counter 241 at a count that indicates the tube 20 (FIGS. 1, 3 and 6) should be replaced. When the number of pulses from the cycle signal generator 11 reaches the preset number, the counter 241 supplies a signal to the resettable switch 243 which applies a signal from the source of voltage 255 to the warning light 253. The resettable switch 243 can be manaully reset when the tube is changed and it resets the counter 241 and disconnects the power 255 from the warning light 253.

To permit a hardware determination of the direction of rotation, the switch 247 receives pulses from the conductor 13 and a direction signal from the cycle signal generator 11 to switch from one of the two output conductors 249 or 251 to the other so that pulses representing the number cycles in each direction can be determined. This function can also be performed in software.

In FIG. 29, there is shown a functional flow diagram of the program for positioning the distributor arm including the step 452 of getting a request to deposit a sample at a particular location, calibrating the system, or updating the position indication of the distributor arm. With this arrangement, the position of the distributor arm is continually updated to ensure that any movement of the arm between intentional moves is tracked. A full rotation of the distributor arm results in 1200 state changes of the optical interrupters described in FIG. 18.

To calibrate the distributor arm, the step 454 of calibrating includes the steps 460 of moving to stop past the last bottle, the step 462 of moving to stop past the first bottle and calculating the total arm flexure, the step 464 of obtaining the time to go from bottle five to bottle one of the 24 bottle base as shown in step 464, the step 466 of getting the time to go from bottle 20 to bottle 24 of the 24 bottle base as shown in step 466, the step 468 of assigning a portion of the total arm flexure to the bottle one side, and the step 470 of moving to bottle one in the order stated. In this manner, a measure is taken of the air at the stop positions caused by flexing of the stop member 272 against the stop 274 (FIG. 7) at bottle positions one and the last bottle position.

The step 456 of going to a bottle includes the step 472 of calculating the target position which factors in expected coast and mechanical play, the step 474 of moving the distributor arm through the required number of change of states as indicated by the optical interrupter, followed by the step 476 of hunting for the correct position necessary followed by the step 478 of updating the coast amount which includes 70 percent of the old value and 30 percent of the new value. The step of hunting for the correct position relates to the ability to detect overshooting by detecting a greater number of pulses than the desired position indicates. If the distributor has been moved, the position must be updated from the information indicating its current position.

The control module 103 initiates all communications through the computer 12 with the modules 202 (FIG. 2). The identification of the module is stored in memory. The modules take readings and convert the readings to engineering units. They respond to requests made by the control module 103 (FIG. 2).

To perform random sampling, the program run time is entered in hours and minutes at the keyboard. The number of samples to be taken during the run time is entered into the keyboard for a one bottle configuration, but the computer program calculates the number of samples from the distribution information for multiple bottle configurations. The program start time is entered as a delay past the run request or clock time and day of the week at the keyboard.

At the time of running, a set of random numbers is generated. These random numbers are scaled so that the sum of the resulting set of time intervals equals the program run time. Specific clock times are then calculated from the random intervals. While the program is running, samples are taken as each of the random clock time occurs at the position indicated by the generated number. The sample bottles for depositing can be obtained by inquiring at memory. Moreover, the software can be drawing and inserting samples into containers in accordance with one program and nonetheless simultaneously follow at least one other sampling program. The other program or programs may be triggered during the execution of the first to start program, such as for example, by the detection of a preprogrammed value of pH or flow rate.

During sampling, the controller runs the pump in reverse to purge the intake line. When configured for one bottle, the controller keeps track of how long the liquid presence signal exists while doing its post-sample purge. This time is indicated by pulses measured by the sensor. If this time measured in pump counts is greater than or equal to a full-threshold, a bottle-full condition is declared. If the count is less than the full-threshold an average of the most recent five readings is found.

At the program run time, the full-threshold is initialized to 200 (large enough to eliminate false bottom-full indications). For each consecutive sample, the full-threshold is set to the average as calculated above plus a pad of 20. The pad value of 20 counts (approximately 20 ml) is added to prevent a premature declaration of a bottle-full condition. Because of variations in sampling conditions, a minimum sample volume of approximately 40 ml is required for this indicator to work reliably.

From the above description, it can be understood that the pumping system of this invention has several advantages, such as for example: (1) it permits higher pumping velocities under high head conditions with peristaltic pumps; (2) it provides longer life to peristaltic pump tubes; (3) it increases the life of tubes and reduces lateral movement; (4) it permits more precise positioning of the distributor outlet port; (5) it permits easy attachment of modules for cooperation with the sampler; (6) it permits safe and easy access to the pump tube for replacement thereof; and (7) it provides a security system to avoid tampering with samples.

Although a preferred embodiment has been described with some particularity, many modifications and variations of the preferred embodiment can be made without deviating from the invention. Therefore, it is to be understood that, within the scope of the appended claims, the invention may be practiced other than as specifically described.

What is claimed is:

1. An apparatus for drawing samples into a plurality of containers comprising:

a peristaltic pump;

a plurality of containers;

means for drawing samples with the peristaltic pump;

a distributor;

means for selecting a designated container by calibrating a distributor arm as to position;

a computer having a memory;

means for moving the distributor arm to the desired container by counting changes in incremental angular movement of the distributor arm until it is over the container;

means for causing at least one sample to flow to the designated container by rotating the distributor over the container and receiving a liquid for depositing into the container;

means for continually updating the position of the distributor arm in memory, a stop member;

means for rotating the arm against the stop member in a first direction;

means for rotating the arm against the stop member in a second direction;

means for calculating an amount in excess of 360 degrees of the motion of the distributor arm caused by a flexing of the stop member; and means for correcting for the excess motion.

2. An apparatus for drawing samples into a plurality of containers comprising:

a peristaltic pump;

a plurality of containers;

means for drawing samples with the peristaltic pump;

a distributor;

means for selecting a designated container by calibrating a distributor arm as to position;

a computer having a memory;

means for moving the distributor arm to the desired container by counting changes in incremental angular movement of the distributor arm until it is over the container;

means for causing at least one sample to flow to the designated container by rotating the distributor over the container and receiving a liquid for depositing into the container;

a random number generator;

means for moving a distributor outlet at designated times over the containers in a random order in accordance with an output of said random number generator to deposit samples; and means for recording the order of samples deposited into the containers.

3. An apparatus for drawing samples into a plurality of containers comprising:

a peristaltic pump;

a plurality of containers;

means for drawing samples with the peristaltic pump;

a distributor;

means for selecting the designated container by calibrating a distributor arm as to position;

a computer having a memory;

means for moving the distributor arm to the desired container by counting changes in incremental angular movement of the distributor arm until it is over the container;

means for causing at least one sample to flow to the designated container by rotating the distributor over the container and receiving a liquid for depositing into the container; and means for continually updating the position of the distributor arm in memory;

a random number generator;

means for moving a distributor outlet at random times over designated containers in accordance with an output of said random number generator to deposit samples; and means for recording the time samples are deposited into the designated containers.

4. An apparatus for drawing samples into a plurality of containers comprising:

a peristaltic pump;

a plurality of containers;

means for drawing samples with the peristaltic pump;

a distributor;

means for selecting a designated container by calibrating a distributor arm as to position;

a computer having a memory;

means for moving the distributor arm to the desired container by counting changes in incremental angular movement of the distributor arm until it is over the container;

means for causing at least one sample to flow to the designated container by rotating the distributor over the container and receiving a liquid for depositing into the container;

means for continually updating the position of the distributor arm in memory;

said peristaltic pump comprising a motor, at least one roller driven by the motor, raceway means for receiving a peristaltic pump tube in a circular recess, means for holding the peristaltic pump tube in the path of said at least one roller when pumping and means for supporting the surface of said at least one roller so as to prevent said at least one roller from compressing said tube more than the thickness of the walls of the tube;

said means for holding the peristaltic pump tube including rotatable means moving in conjunction with said at least one roller to hold said peristaltic pump tube in the path of said at least one roller.

* * * * *